United States Patent
Namane et al.

(10) Patent No.: US 8,530,473 B2
(45) Date of Patent: Sep. 10, 2013

(54) TETRAHYDROQUINOXALINE UREA DERIVATIVES AS MODULATORS OF 11β-HYDROXYSTEROID DEHYDROGENASE TYPE 1

(75) Inventors: Claudie Namane, Paris (FR); Eric Nicolai, Paris (FR); Francois Pacquet, Paris (FR); Cecile Pascal, Paris (FR); Olivier Venier, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/386,827

(22) PCT Filed: Jul. 23, 2010

(86) PCT No.: PCT/FR2010/051564
§ 371 (c)(1),
(2), (4) Date: Feb. 15, 2012

(87) PCT Pub. No.: WO2011/012801
PCT Pub. Date: Feb. 3, 2011

(65) Prior Publication Data
US 2012/0135958 A1    May 31, 2012

(30) Foreign Application Priority Data
Jul. 27, 2009 (FR) ..................................... 09 03687

(51) Int. Cl.
*A61K 31/495* (2006.01)
(52) U.S. Cl.
USPC ........ 514/249; 544/355; 544/359; 546/268.1; 548/131; 548/250
(58) Field of Classification Search
USPC .............. 514/249; 544/355, 359; 546/268.1; 548/131, 250
See application file for complete search history.

(56) References Cited

FOREIGN PATENT DOCUMENTS

| | | | |
|---|---|---|---|
| CA | 2713367 | * | 9/2009 |
| WO | WO2008/000950 A2 | | 1/2008 |
| WO | WO2008/000951 A2 | | 1/2008 |
| WO | WO2009/112691 A2 | | 9/2009 |

OTHER PUBLICATIONS

Jordan, V. C. Nature Reviews: Drug Discovery, 2, 2003, 205.*
Hackam, et al. JAMA, 296(14), 2006, 1731-1732.*
Vippagunta, et al. Advanced Drug Delivery Reviews, 48, 2001, 18.*
Hughes, Katherine et al., "11-Beta-hydroxysteroid dehydrogenase type 1 (11Beta-HSD1) inhibitors in Type 2 diabetes mellitus and obesity," Expert Opinion on Investigational Drugs (2008), vol. 17, No. 4, pp. 481-496.
Saiah, Eddine, "The Role of 11Beta-Hydroxysteroid Dehydrogenase in Metabolic Disease and Therapeutic Potential of 11Beta-HSD1 Inhibitors," Current Medicinal Chemistry (2008), vol. 15, pp. 642-649.
International Search Report dated Oct. 14, 2010 issued in PCT/FR2010/051564.

* cited by examiner

*Primary Examiner* — Douglas M Willis
(74) *Attorney, Agent, or Firm* — Scully, Scott, Murphy & Presser, P.C.

(57) ABSTRACT

The invention relates to a compound of the general formula (I),

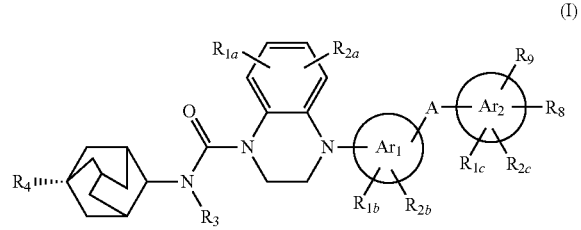

as defined herein which is useful in modulating the activity of 11β-hydroxysteroid dehydrogenase type 1 (11βHSD1) and are useful for treating pathologies in which such modulation is beneficial, as in the case of metabolic syndrome or of noninsulin-dependent type 2 diabetes. The invention also relates to pharmaceutical preparations containing such a compound, processes for preparing and intermediates useful in the preparation of a such a compound.

18 Claims, No Drawings

TETRAHYDROQUINOXALINE UREA DERIVATIVES AS MODULATORS OF 11β-HYDROXYSTEROID DEHYDROGENASE TYPE 1

BACKGROUND OF THE INVENTION

The present invention relates to tetrahydroquinoxaline urea derivatives, preparation thereof, and therapeutic use thereof.

FIELD OF THE INVENTION

The compounds according to the invention modulate the activity of 11β-hydroxysteroid dehydrogenase type 1 (11βHSD1) and are useful for treating pathologies in which such modulation is beneficial, as in the case of metabolic syndrome or of noninsulin-dependent type 2 diabetes.

DESCRIPTION OF THE RELATED ART

11βHSD1 locally catalyzes the conversion of inactive glucocorticoids (cortisone in humans) to active glucocorticoids (cortisol in humans) in various tissues and organs, principally the liver and adipose tissue, but also in muscles, bone, pancreas, endothelium, ocular tissue and in certain parts of the central nervous system. 11βHSD1 acts as a regulator of the action of glucocorticoids in the tissues and organs where it is expressed (Tomlinson et al., Endocrine Reviews 25(5), 831-866 (2004), Davani et al., J. Biol. Chem. 275, 34841 (2000); Moisan et al., Endocrinology, 127, 1450 (1990)).

The principal pathologies in which glucocorticoids and inhibition of 11βHSD1 are involved are stated below.

A. Obesity, Type 2 Diabetes and Metabolic Syndrome

The role of 11βHSD1 in obesity, type 2 diabetes and metabolic syndrome (also known as syndrome X or insulin resistance syndrome) where the symptoms include visceral obesity, glucose intolerance, insulin resistance, hypertension, type 2 diabetes and hyperlipidemia (Reaven Ann. Rev. Med. 44, 121 (1993)) is described in many works. In humans, treatment with carbenoxolone (a nonspecific inhibitor of 11βHSD1) improves insulin sensitivity in slender volunteer patients and in patients with type 2 diabetes (Andrews et al., J. Clin. Endocrinol. Metab. 88, 285 (2003)). Moreover, mice whose gene for 11βHSD1 has been turned off are resistant to hyperglycemia induced by stress and obesity, show attenuation of the induction of liver enzymes of neoglucogenesis (PEPCK and G6P) and display an increase in insulin sensitivity in adipose tissue (Kotelevstev et al., Proc. Nat. Acad. Sci. 94, 14924 (1997); Morton et al., J. Biol. Chem. 276, 41293 (2001)). Moreover, transgenic mice in which the gene for 11βHSD1 has been overexpressed in adipose tissues have a phenotype similar to that of human metabolic syndrome (Masuzaki et al., Science 294, 2166 (2001)). It should be noted that the phenotype observed exists without an increase in total circulating glucocorticoids, but is induced by specific increase in active glucocorticoids in the adipose deposits. Furthermore, new classes of specific inhibitors of 11βHSD1 have appeared recently:

arylsulfonamidothiazoles have been shown to improve insulin sensitivity and reduce the level of glucose in the blood of mice with hyperglycemia (Barf et al., J. Med. Chem. 45, 3813 (2002)). Moreover, it was shown in a recent study that compounds of this type reduced food intake as well as weight gain in obese mice (Wang et al. Diabetologia 49, 1333 (2006));

triazoles have been shown to improve metabolic syndrome and slow the progression of atherosclerosis in mice (Hermanowski-Vosatka et al., J. Exp. Med. 202, 517 (2005)).

A2. Microvascular Complications of Diabetes

The presence of chronic complications in patients with type 2 diabetes is often linked to the severity and duration of diabetes. Functional and structural microvascular disorders largely explain the development of certain pathologies observed in diabetic patients such as neuropathy, retinopathy, and nephropathy (Rayman, Diabetes Review 7:261-274, 1999; Gärtner and Eigentler, Clin Nephrol 70:1-9, 2008; Zent and Pozzi, Sem Nephrol 27:161-171, 2007; Malecki et al., EJCI38:925-930, 2008). Chronic increase in glycemia, or glucose intolerance, represent major risk factors of these microvascular complications (Robinson Singleton et al. Diabetes 52:2867-2873, 2003; Lachin et al. Diabetes 57: 995-1001, 2008). By providing better control of glycemia, through a decrease in hepatic neoglucogenesis and an increase in the body's insulin sensitivity (see chapter "obesity, type 2 diabetes and metabolic syndrome"), inhibitors of 11βHSD1 can prevent progression to the microvascular complications observed in diabetic patients. However, strict control of glycemia cannot completely prevent the development of microvascular complications, and it is therefore necessary to discover new treatments for more general treatment of diabetic and dyslipidemic patients (Girach et al. Int J Clin Pract 60(11): 1471-1483, 2006; Taylor. Curr Diab Rep 8 (5): 345-352; 2008). Interestingly, a study by Chiodini et al. (Diabetes Care 30: 83-88, 2007) showed that cortisol secretion in diabetic patients was linked directly to the presence of chronic macrovascular or microvascular complications. Moreover, microvascular reactivity and endothelial function are altered in patients with Cushing syndrome who have hypercortisolism (Prazny et al. Physiol Rev 57:13-22, 2008).

More particularly, Bhatia et al. (Ann Ophthalmol 15:128-130; 1983) demonstrated a link between raised plasma cortisol levels and retinopathy in diabetic patients.

Koh et al. showed that treatment of patients with Cushing syndrome by adrenalectomy, making it possible to reverse hypercortisolism, improves renal function.

The clinical parameters of polyneuropathies (sensory perception, cardiac autonomic neuropathy) are associated with an increase in cortisol secretion in diabetic patients (Tsigos et al. J Clin Endocrinol Metab 76:554-558, 1993).

All these elements show that a decrease in the impact of cortisol by local inhibition of its regeneration, via inhibitors of 11βHSD1, could have a favorable role in microcirculatory disorders associated with diabetes (polyneuropathy, retinopathy, and nephropathy).

B. Cognition and Dementia

Mild cognitive disorders are phenomena that are common to the elderly and to type 1 and 2 diabetics, and can gradually lead to depression or dementia (Messier et al., Neurobiol. aging 26, 26; Greenwood et al. (2005), Neurobiol. aging 26, 45 (2005)). Both in older animals and older humans, interindividual differences for general cognitive functions have been linked to differences in long-term exposure to glucocorticoids (Lupien et al., Nat. Neurosci. 1, 69, (1998)). Moreover, deregulation of the HPA (hypothalamic-pituitary-adrenal) axis, resulting in chronic exposure of certain sub-regions of the brain to glucocorticoids has been suggested as contributing to the decline of cognitive functions (McEwen et al., Curr. Opin. Neurobiol. 5, 205, 1995). 11βHSD1 is abundant in the brain and is expressed in many sub-regions including the hypothalamus, the frontal cortex and the cerebellum (Sandeep et al., Proc. Natl. Acad. Sci. 101, 6734 (2004)).

Mice deficient in 11βHSD1 are protected against the dysfunctions of the hypothalamus associated with glucocorticoids that are linked to old age (Yau et al., *Proc. Natl. Acad. Sci.* 98, 4716, (2001)). Moreover, in studies in humans, it has been shown that administration of carbenoxolone improves verbal fluency and verbal memory in the elderly (Yau et al., *Proc. Natl. Acad. Sci.* 98, 4716 (2001), Sandeep et al., *Proc. Natl. Acad. Sci.* 101, 6734 (2004)). Finally, the use of selective inhibitors of 11βHSD1 of the triazole type has shown that they prolong memory retention in older mice (Rocha et al., Abstract 231 *ACS meeting*, Atlanta, 26-30 Mar. 2006). Moreover, it was shown in diabetic rodent models that the corticosterone level contributed to the development of cognitive pathologies induced by diabetes (Stranhan et al., Nature neurosc. 11, 309 (2008)). Thus, inhibitors of 11βHSD1, by allowing a reduction in cortisol regeneration in the hippocampus, could have a beneficial effect on cognitive functions in elderly diabetic patients (Sandeep et al., *Proc. Natl. Acad. Sci.* 101, 6734 (2004)).

C. Intraocular Pressure

Glucocorticoids can be used topically or systemically for a wide range of pathologies of clinical ophthalmology. A particular complication of these treatments is glaucoma induced by the use of corticosteroids. This pathology is characterized by increase in intraocular pressure (IOP). In the most severe cases and for untreated forms, IOP can lead to a partial loss of visual field and possibly to complete loss of sight. IOP is the result of an imbalance between production of aqueous humor and drainage thereof. The aqueous humor is produced in nonpigmented epithelial cells and drainage is performed by the cells of the trabecular network. 11βHSD1 is localized in the nonpigmented epithelial cells and its function is clearly amplification of the activity of glucocorticoids in these cells (Stokes et al., *Invest. Ophthalmol. Vis. Sci.* 41, 1629 (2000)). This concept is confirmed by the observation that the concentration of free cortisol is greatly in excess relative to cortisone in the aqueous humor (ratio 14/1). The functional activity of 11βHSD1 in the eyes was evaluated by studying the effects of carbenoxolone in healthy volunteers. After seven days of treatment with carbenoxolone, IOP is reduced by 18% (Rauz et al., *Invest. Ophtamol. Vis. Sci.* 42, 2037 (2001)). The inhibition of 11βHSD1 in the eyes is therefore predicted as reducing the local concentration of glucocorticoids and the IOP, producing a beneficial effect in the treatment of glaucoma and other disorders of vision.

D. Hypertension

Hypertensive substances from the adipocytes such as leptin and angiotensinogen have been suggested as being key elements in obesity-related hypertension pathologies (Wajchenberg et al., *Endocr. Rev.* 21, 697 (2000)). Leptin, which is secreted in excess in aP2-11βHSD1 transgenic mice (Masuzaki et al., *J. Clinical Invest.* 112, 83 (2003)), can activate various networks of sympathetic neuronal systems, including those that regulate arterial pressure (Matsuzawa et al., *Acad. Sci.* 892, 146 (1999)). Moreover, the renin-angiotensin system (RAS) has been identified as being a determining pathway in the variation of arterial pressure. Angiotensinogen, which is produced in the liver and in adipose tissue, is a key substrate for renin and is at the origin of activation of the RAS. The plasma angiotensinogen level is significantly raised in aP2-11βHSD1 transgenic mice, as are those of angiotensin II and of aldosterone (Masuzaki et al., *J. Clinical Invest.* 112, 83 (2003)); these elements lead to the increase in arterial pressure. Treating these mice with low doses of an angiotensin II receptor antagonist eliminates this hypertension (Masuzaki et al., *J. Clinical Invest.* 112, 83 (2003)). These data illustrate the importance of local activation of glucocorticoids in adipose tissue and in the liver, and suggests that this hypertension may be caused or exacerbated by the activity of 11βHSD1 in these tissues. Inhibition of 11βHSD1 and reduction of the level of glucocorticoids in adipose tissue and/or in the liver is therefore predicted as having a beneficial role for the treatment of hypertension and of related cardiovascular disorders.

D2. Salt-Sensitive Arterial Hypertension

It is estimated that about 30 to 50% of the general population are particularly sensitive to salt. There is a wealth of evidence suggesting a link between sensitivity to salt and arterial hypertension and cardiovascular risks (Weinberger M H, Curr Opin Cardiol 2004; 19:353-356). It has been shown that salt-sensitive subjects have a decreased variability of heart rate, as well as increased arterial pressure and cortisol production during mental stress, compared with subjects who are not sensitive (Weber C S et al., Journal of Human Hypertension 2008; 22:423-431). Moreover, a recent study by Liu Y et al. (Physiol Genomics 2008 Sep. 30) demonstrated in the Dahl salt-sensitive rat that specific inhibition of expression of renal medulla 11βHSD1, by the use of shRNA, can greatly reduce, in animals, the increase in mean arterial pressure induced by a salty diet. These elements suggest that an inhibitor of the enzyme 11βHSD1 would very probably have a beneficial effect on this form of arterial hypertension.

E. Osteoporosis

The development of the skeleton and the osseous functions are also regulated by the action of glucocorticoids. 11βHSD1 is present in osteoclasts and osteoblasts. Treatment of healthy volunteers with carbenoxolone showed a decrease in markers of bone resorption without a change in the markers of bone formation (Cooper et al., Bone, 27, 375 (2000)). Inhibition of 11βHSD1 and reduction of the level of glucocorticoids in the bones could therefore be used as a protective mechanism in the treatment of osteoporosis.

F. Lipodystrophy Associated with Highly Active Antiretroviral Therapy (HAART), or HAL Syndrome The use of intensive antiretroviral treatment for AIDS patients often induces a lipodystrophy syndrome (HAL) resembling Cushing syndrome, and associating increase in abdominal fat mass, hypertriglyceridemia and insulin resistance. It has been shown (Sutinen et al., Diabetologia, 47, 1668 (2004)) that this lipodystrophy (HAL) is associated with an increase in expression of 11βHSD1 in patients' adipose tissue. Inhibitors of 11βHSD1, allowing a reduction of cortisol regeneration in the adipose tissue, could therefore have a beneficial role in patients with lipodystrophy associated with intensive treatment of AIDS with antiretrovirals (HAL syndrome).

G. Infectious Diseases

Certain infections, such as tuberculosis, are associated with disorders of the immune response (Ellner J J, J. Lab. Clin. Med, 130, 469, (1997)). This feature, which is most often accompanied by an increase in secretion of certain cytokines (IL-10, INFα) and/or response to certain cytokines, seems to be caused, at least partly, by local tissue exposure of the immune cells to glucocorticoids. Moreover, the administration of synthetic glucocorticoids in humans or animals causes reactivation of tuberculosis in humans and in animals (Haanas O C et al. Eur. J. Respir. Dis. 64, 294 (1998), Brown et al. Infect. Immun. 63, 2243, (1995)). Moreover, various stresses that are activators of the HPA axis lead to reactivation of said infection.

Apart from these particular cases, circulating glucocorticoid levels as well as activation of the HPA axis seem to be normal in patients with tuberculosis (Baker et al. Am. J. Resp. Crit. Care. Med., 162, 1641 (2000)). In contrast, the levels of cortisol versus cortisone in the bronchioalveolar fluid seem to be raised, reflecting a modulation of glucocorticoid metabolism to the active form (notably dependent on the activity of 11βHSD1). Inhibition of 11βHSD1 in the peripheral tissues and notably the lungs might consequently produce a beneficial effect on stabilization and then reversion of infection.

H. Cardiac Hypertrophy and Heart Failure

Cardiovascular diseases represent the primary cause of morbidity and mortality in the industrialized countries, and left ventricular hypertrophy (LVH) is an independent risk factor of cardiovascular mortality (Havranek E P, Am J Med 121:870-875, 2008). Aside from genetic causes, pathological conditions such as arterial hypertension, myocardial infarction, or renal insufficiency can lead to a compensatory hypertrophy, subsequently progressing to chronic heart failure. 11βHSD1 activity, permitting conversion of 11-dehydrocorticosterone to corticosterone, is expressed in the cardiomyocytes of newborn rats, and contributes to the modulating activity of glucocorticoids and aldosterone in the heart (Sheppard and Autelitano, Endocrinology 143:198-204, 2002). Using these cells, Lister et al. (Cardiovascular Research 70: 555-565, 2006) showed that drug-induced hypertrophy of the cardiomyocytes is accompanied by an increase in activity of the enzyme 11βHSD1. In this same study, the use of RU-486, a specific antagonist of the glucocorticoid receptors, made it possible to reduce the hypertrophy of the cells.

Inhibitors of 11βHSD1 activity might therefore limit cardiac hypertrophy and thus prevent progression to heart failure.

I. Liver Diseases:

I1. Hepatic Steatosis:

Studies in severely obese patients (BMI>35 kg/m2) report a prevalence of 91% for steatosis and of 37% for steatohepatitis (Neuschwander-Tetri & Caldwell, *Hepatology*, 37, 1202-1219, 2003). Type 2 diabetes is another major factor associated with steatosis with a prevalence of 70% reported for a sample of 3000 Italian diabetics (Targher et al., *Diabetes Care*, 30, 1212-1218, 2007). Moreover, a link has been observed between insulin resistance and hepatic steatosis independently of obesity in patients with nonalcoholic hepatic steatosis (Manchesini et al., *Diabetes*, 50, 1844-1850, 2001). In obese patients, 11βHSD1 activity appears to be modified, as indicated by the activation of orally administered cortisone, urinary excretion of cortisol metabolites or hepatic tissue expression of 11βHSD1. (Tomlinson et al., *Endocrine Rev*, 25, 831-866, 2004; Rask et al., *J. Clin. Endocrin. Metab.*, 86, 1418-1421, 2001; Stewart et al., *J. Clin. Endocrin. Metabol.* 84, 1022-1027, 1999; Valsamakis et al., *J. Clin. Endocrinol. Metabol.*, 89, 4755-4761, 2004). Transgenic mice overexpressing 11βHSD1 in the adipose tissue or in the liver develop hepatic steatosis and dyslipidemia (Masuzaki et al., *Sciences* 294, 2166-2170, 2001; Paterson et al., *PNAS*, 101, 7088-7093, 2004). Inhibition of 11βHSD1 in the rat reduces fasting triglyceridemia following a decrease in secretion of hepatic triglycerides and an increase in capture and tissue oxidation of fatty acids, which is also reflected in the liver by a significant decrease in triglycerides (Berthiaume et al., *Am. J. Physiol. Endocrinol. Metab.*, 293, 1045-1052, 2007). Local reduction of active glucocorticoid by inhibition of 11βHSD1 activity is therefore envisaged for reducing the insulin-resistant and lipid effects of glucocorticoids and thus reducing hepatic steatosis.

I2. Metabolic Steatohepatitis:

Metabolic steatohepatitis represents a stage of development of metabolic hepatic steatosis in some people. A correlation has been described between urinary cortisol, post-dexamethasone cortisol concentration and the grade of necroinflammation and hepatic fibrosis in subjects with metabolic steatohepatitis suggesting the existence of subclinical or local hypercorticolism (Targher et al., *Clin. Endocrinol.*, 64, 337-341, 2006). A general and local correction (at centrilobular level) of insulin resistance, and an improvement in oxidation of hepatic fatty acids by inhibition of 11βHSD1 activity, as well as reduction of the pro-fibrotic effects of cortisol, are therefore predictive of an improvement of the pathological evolution.

I3. Hepatic Regeneration:

The liver has a considerable capacity for regeneration, completely necessary in the case of injuries whether or not of infectious origin, in particular arising from the digestive tract. For example, hepatic apoptosis or necrosis can result from drug-induced, viral, alcoholic, metabolic, cholestatic or vascular ischemic toxicity. The glucocorticoids inhibit hepatocyte proliferation and hepatic tissue regeneration (Tsukamoto & Kojo, *Gut*, 30, 387-390, 1989; Nagy et al., *Hepatology*, 28, 423-429, 1998; Tannuri et al., *Pediatr. Transplantation*, 12, 73-79, 2008). Inhibition of 11βHSD1 reductase activity could in this context lessen the negative local effects of cortisol on hepatic regeneration and are to be aligned with the pro-angiogenic effects of these inhibitors and with their positive action on certain growth factors.

J. Healing of Chronic Skin Wounds:

The healing of chronic wounds depends on the underlying pathological context which modifies and desynchronizes the physiological stages of healing. In chronic diabetic ulcer, the potential benefit of inhibitors of 11βHSD1 is to be seen both in correction of the manifestations of diabetes, taking into account the local pathological role of endogenous corticoids at the level of the wound and the state of pathological progression. There is some evidence showing that endogenous corticoids are directly involved in the alteration of wound healing in humans and in rodent animal models (Goforth et al., *J. Foot Surgery*, 19, 199-2002, 1980; Dostal et al., *Arch. Surg*, 125, 636-640, 1990; Bitard, *Am. J. Pathology*, 152, 547-554, 1998). Local production of cortisol is predicted by the presence of 11βHSD1 reductase activity at endothelial, fibroblastic, and cutaneous level in humans and in rodents (Gong et al., *Steroids* 73, 1187-1196, 2008; Hammami et al., *J. Clin. Endocrinol. Metabol.*, 73, 326-334, 1991; Cooper et al., *ENDO* 2003; Teelucksingh et al., *Lancet*, 335, 1060-1063, 1990). Cortisol and other glucocorticoids inhibit skin ulcer healing by many mechanisms and at different stages: alteration of microcirculatory vasomotor activity, inhibition of the inflammatory phase in particular on the synthesis of prostaglandins, of leukotrienes, of cytokines, such as TNFalpha and production of IL-1beta, IL-4, etc. and signalling of IFN-gamma, increase of infection, reduction of cellular motility and proliferation of keratinocytes, reduction of expression of pro-angiogenic factors such as VEGF, suppression of expression of TGFbeta 1 and 2 that are essential in the production of collagen by the fibroblasts and their transformation into myofibroblasts, suppression of expression of MMP1, 2, 9 and 10 and induction of TIMP thus blocking remodelling, promotion of terminal epidermal differentiation but inhibition of the first stages of differentiation, causing fragility of the epidermis (Bitard, *Am. J. Pathology*, 152, 547-554, 1998, Beer et al., *Vitam. Horm.*, 59, 217-239, 2000; Rosen & Miner, *Endocrine Review*, 26, 452-464, 2005, Stojadinovic et al., *J. Biol. Chem*, 282, 4021-4034, 2007). Conversely, and as expected, inhibition of 11βHSD1 reductase activity is described as inducing vasodilatation, a pro-angiogenic and anti-infectious effect (see the corresponding chapters) and in certain inflammatory situations, producing exacerbation and growth factor overexpression such as TGF-beta (Zhang et al., *J. Immunology*, 179, 6325-6335, 2007). Inhibitors of 11βHSD1 should therefore, based on this action, improve the healing of chronic skin wounds.

BRIEF SUMMARY OF THE INVENTION

Tetrahydroquinoxaline urea derivatives have now been found, which have an adamantane nucleus, and which modulate the activity of 11βHSD1.

DETAILED DESCRIPTION OF THE INVENTION

The present invention relates to compounds corresponding to formula (I):

$$\text{(I)}$$

in which:
A represents a bond, an oxygen atom or an —O—CH$_2$— group,
Ar$_1$ represents a phenyl or heteroaryl group,
Ar$_2$ represents a phenyl group, a heteroaryl group or a heterocycloalkyl group,
R$_{1a,b,c}$ and R$_{2a,b,c}$, which may be identical or different, each represent a hydrogen or halogen atom or an alkyl group; cycloalkyl optionally substituted with an alkyl, haloalkyl, alkoxy-alkyl, alkoxy-haloalkyl or —COOR$_5$ group; -alkyl-cycloalkyl optionally substituted with one or more halogen atoms; —OR$_5$ (hydroxy or alkoxy); hydroxy-alkyl; alkoxy-alkyl; alkoxy-alkoxy; haloalkyl; —O-haloalkyl; oxo; —CO-alkyl; —CO-alkyl-NR$_6$R$_7$; —CO-haloalkyl; —COOR$_5$; alkyl-COOR$_5$; —O-alkyl-COOR$_5$; —SO$_2$-alkyl; —SO$_2$-cycloalkyl; —SO$_2$-alkyl-cycloalkyl; —SO$_2$-alkyl-OR$_5$; —SO$_2$-alkyl-COOR$_5$; —SO$_2$-alkyl-NR$_6$R$_7$; —SO$_2$-haloalkyl; alkyl-SO$_2$-alkyl; —SO$_2$—NR$_6$R$_7$; —SO$_2$-alkyl-alkoxy-alkoxy; —CONR$_6$R$_7$; -alkyl-CONR$_6$R$_7$ or —O-alkyl-NR$_6$R$_7$, or R$_{1a}$, R$_{1b}$, R$_{1c}$ are bound respectively to R$_{2a}$, R$_{2b}$, R$_{2c}$ and to the carbon atom that bears them and represent —O-alkyl-O—;
R$_3$ represents a hydrogen atom or an alkyl group,
R$_4$ represents a hydrogen or halogen atom or a cyano, —OR$_5$, hydroxy-alkyl, —COOR$_5$, —NR$_6$R$_7$, —CONR$_6$R$_7$, —SO$_2$-alkyl or —SO$_2$—NR$_6$R$_7$, —NR$_6$—COOR$_5$, —NR$_6$—COR$_5$, —CO—NR$_6$-alkyl-OR$_5$ group;
R$_5$, R$_6$ and R$_7$, which may be identical or different, each represent a hydrogen atom, an alkyl group or an -alkyl-phenyl group, and
R$_8$ represents an alkyl, alkyl-Si(alkyl)$_3$; —SO$_2$-alkyl-Si (alkyl)$_3$; phenyl; alkoxy-imino group; alkyl-cycloalkyl optionally substituted with one or more halogen atoms; heterocycloalkyl substituted with one or more halogen atoms, one or more hydroxyl or hydroxy-alkyl groups; or else R$_8$ and R$_9$, together with the carbon atom to which they are bound, form a cycloalkyl group optionally substituted with one or more halogen atoms or one or more carboxyl groups;

R$_9$ represents a hydrogen atom or an alkyl group; provided that when R$_8$ is an alkyl group, it is attached to the silicon atom of a group Ar$_2$.

The compounds of formula (I) can have one or more asymmetric carbon atoms. They can therefore exist in the form of enantiomers or of diastereoisomers. These enantiomers, diastereoisomers, and mixtures thereof, including the racemic mixtures, form part of the invention.

The compounds of formula (I) can be in the form of bases or of acids or can be salified by acids or bases, notably pharmaceutically acceptable acids or bases. These salts of addition form part of the invention. These salts are advantageously prepared with pharmaceutically acceptable acids or bases, but salts of other acids or bases that can be used, for example, for purifying or isolating the compounds of formula (I), also form part of the invention.

The compounds of formula (I) can also exist in the form of hydrates or solvates, namely in the form of associations or combinations with one or more solvent molecules. These solvates also form part of the invention.

In the context of the present invention, and unless stated otherwise in the text, the terms used have the following meanings:
a halogen atom: a fluorine, a chlorine, a bromine or an iodine;
an alkyl group: a saturated, linear or branched aliphatic group having from 1 to 5 carbon atoms. As examples, we may mention the methyl, ethyl, propyl, methylpropyl, isopropyl, butyl, isobutyl, tertbutyl or pentyl groups;
a cycloalkyl group: a cyclic alkyl group having from 3 to 6 carbon atoms. As examples, we may mention the cyclopropyl, cyclobutyl, cyclopentyl groups;
an alkoxy group: a radical of formula —O-alkyl, where the alkyl group is as defined above;
a hydroxy-alkyl group: a radical of formula alkyl-OH, where the alkyl group is as defined above;
an alkoxy-alkyl group: a radical of formula alkyl-O-alkyl, where the alkyl groups, which may be identical or different, are as defined above. As examples, we may mention —(CH$_2$)$_2$—O—CH$_3$, —(CH$_2$)$_3$—O—CH$_3$, —CH—(CH$_2$—O—CH$_3$)$_2$;
an alkoxy-alkoxy group: a radical of formula —O-alkyl-O-alkyl, where the alkyl groups, which may be identical or different, are as defined above;
a haloalkyl group: an alkyl group as defined above substituted with 1 to 5 halogen atoms, as defined above. We may mention for example the trifluoromethyl group;
a heteroaryl group: an aromatic group comprising 5 to 9 atoms, including 1 to 3 heteroatoms, such as nitrogen, oxygen or sulfur. We may notably mention the pyridinyl, pyrimidinyl, pyridazinyl or thiazolyl groups; and
a heterocycloalkyl: a mono-, bi-cyclic alkyl group, optionally bridged, having from 4 to 9 atoms or optionally partially unsaturated and of which 1 or 2 atoms are heteroatoms, such as oxygen, nitrogen, sulfur or silicon. We may notably mention the pyrrolidinyl, piperidinyl, piperazinyl, tetrahydropyranyl, morpholinyl, homopiperazinyl, 3,8-diazabicyclo[3.2.1]octane, thiomorpholinyl and thiomorpholinyl-1,1-dioxide, octahydro-pyrrolo[3,4-c]pyrrole, 1,2,3,6-tetrahydro-pyridine, 2,5-diaza-bicyclo[2.2.1]heptane, azasilinane groups;
a carbonyl function is represented by CO.

In the context of the present invention, R$_{1a,b,c}$ denotes the groups R$_{1a}$, R$_{1b}$ and R$_{1c}$ and R$_{2a,b,c}$ denotes the groups R$_{2a}$, R$_{2b}$ and R$_{2c}$. When Ar$_2$ represents a heterocycloalkyl group, the groups R$_{1c}$, R$_{2c}$, R$_8$ and R$_9$ can be carried by any atom of said heterocycle, whether it is a carbon atom or a heteroatom (for example a nitrogen atom), including by the same atom of said heterocycloalkyl (for example when it is a sulfur atom).

In the compounds of formula (I) according to the invention, the group $R_4$ and the urea group can be in trans position or in cis position. The compounds of formula (I) in which $R_4$ and the urea group are in trans position are particularly preferred.

Among the compounds of formula (I) according to the invention, we may mention a subgroup of compounds in which A represents a bond.

Another subgroup of the compounds of formula (I) according to the invention is such that $Ar_1$ represents a heteroaryl group. Advantageously, $Ar_1$ represents a pyridinyl group.

Another subgroup of the compounds of formula (I) according to the invention is such that $Ar_2$ represents a heterocycloalkyl group. Advantageously, $Ar_2$ represents a piperidinyl, piperazinyl or azasilinanyl group.

Among the compounds of formula (I) according to the invention in which $Ar_1$ represents a phenyl group or a heteroaryl with 6 ring members, we may mention those in which the bond between the nuclei $A-Ar_2$ and $Ar_1$ is in para position relative to the bond between $Ar_1$ and the nitrogen atom of the tetrahydroquinoxaline nucleus to which it is bound.

Among the compounds of formula (I) according to the invention in which $Ar_2$ represents a heteroaryl or heterocycloalkyl group, we may mention those which are bound to group A by a heteroatom.

Another subgroup of the compounds of formula (I) according to the invention is such that $R_{1a,b,c}$ and $R_{2a,b,c}$ each represent a hydrogen atom.

Another subgroup of the compounds of formula (I) according to the invention is such that $R_3$ represents a hydrogen atom.

Another subgroup of the compounds of formula (I) according to the invention is such that $R_4$ represents a hydroxy-alkyl or —$CONH_2$ group.

Another subgroup of the compounds of formula (I) according to the invention is such that $R_8$ represents an alkyl group, alkyl-Si(alkyl)$_3$; —$SO_2$-alkyl-Si(alkyl)$_3$; phenyl; alkoxy-imino; heterocycloalkyl substituted with one or more halogen atoms, one or more hydroxyl or hydroxy-alkyl groups; or else $R_8$ and $R_9$, together with the carbon atom to which they are bound, form a cycloalkyl group optionally substituted with one or more halogen atoms or one or more carboxyl groups; $R_9$ represents a hydrogen atom or an alkyl group; provided that when $R_8$ is an alkyl group, it is attached to the silicon atom of $Ar_2$.

The subgroups defined above taken separately or in combination also form part of the invention.

A group of compounds of formula (I) particularly preferred in the sense of the invention consists of the compounds of formula (I) in which:
A is a direct bond;
$Ar_1$ is a heteroaryl;
$Ar_2$ is a heterocycloalkyl;
$R_3$ represents a hydrogen atom,
$R_4$ represents an OH or —$CONH_2$ group,
$R_8$ represents an alkyl group, alkyl-Si(alkyl)$_3$; —$SO_2$-alkyl-Si(alkyl)$_3$; phenyl; alkoxy-imino; heterocycloalkyl substituted with one or more halogen atoms, one or more hydroxyl or hydroxy-alkyl groups; or else $R_8$ and $R_9$, together with the carbon atom to which they are bound, form a cycloalkyl group optionally substituted with one or more halogen atoms or one or more carboxyl groups;
$R_9$ represents a hydrogen atom or an alkyl group; provided that when $R_8$ is an alkyl group, it is attached to the silicon atom of $Ar_2$.

Advantageously, $R_8$ represents an alkyl group, alkyl-Si(alkyl)$_3$; —$SO_2$-alkyl-Si(alkyl)$_3$; phenyl; alkoxy-imino; pyrrolidinyl substituted with one or more halogen atoms, a hydroxyl or hydroxy-alkyl group; thiomorpholinyl; or else $R_8$ and $R_9$, together with the carbon atom to which they are bound, form a cycloalkyl group optionally substituted with one or more halogen atoms or one or more carboxyl groups; $R_9$ represents a hydrogen atom or an alkyl group provided that when $R_8$ is an alkyl group, it is attached to the silicon atom of $Ar_2$.

Among the compounds of formula (I) according to the invention, we may notably mention the following compounds:

Trans 4-[5-(4-trimethylsilanylmethyl-piperazin-1-yl)-pyridin-2-yl]-3,4-dihydro-2H-quinoxaline-1-carboxylic acid (5-hydroxy-adamantan-2-yl)-amide;

Trans 4-(4-tert-butoxyimino-3,4,5,6-tetrahydro-2H-[1,3']bipyridinyl-6'-yl)-3,4-dihydro-2H-quinoxaline-1-carboxylic acid (5-hydroxy-adamantan-2-yl)-amide;

Trans 4-{5-[4-(2-trimethylsilanyl-ethanesulfonyl)-piperazin-1-yl]-pyridin-2-yl}-3,4-dihydro-2H-quinoxaline-1-carboxylic acid (5-hydroxy-adamantan-2-yl)-amide;

Trans 4-{5-[4-(2,2-difluoro-cyclopropylmethyl)-piperazin-1-yl]-pyridin-2-yl}-3,4-dihydro-2H-quinoxaline-1-carboxylic acid (5-carbamoyl-adamantan-2-yl)-amide;

Trans-6-{6-[4-(5-Carbamoyl-adamantan-2-ylcarbamoyl)-3,4-dihydro-2H-quinoxalin-1-yl]-pyridin-3-yl}-6-aza-spiro[2.5]octane-1-carboxylic acid;

Trans 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;

Trans 4-[4-((R)-2-hydroxymethyl-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;

Trans 4-[4-((S)-2-hydroxymethyl-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;

Trans 4-[4-((S)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;

Trans 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;

Trans 4-[4-(3,3-difluoro-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;

Trans 4-[5-(1,1-difluoro-6-aza-spiro[2.5]oct-6-yl)-pyridin-2-yl]-3,4-dihydro-2H-quinoxaline-1-carboxylic acid (5-carbamoyl-adamantan-2-yl)-amide;

Trans 4-[5-(4-methyl-4-phenyl-[1,4]azasilinan-1-yl)-pyridin-2-yl]-3,4-dihydro-2H-quinoxaline-1-carboxylic acid (5-carbamoyl-adamantan-2-yl)-amide;

Trans 4-[5-(4,4-dimethyl-[1,4]azasilinan-1-yl)-pyridin-2-yl]-3,4-dihydro-2H-quinoxaline-1-carboxylic acid (5-carbamoyl-adamantan-2-yl)-amide.

It should be noted that the above compounds have been named using IUPAC nomenclature by means of the AutoNom software (Beilstein Information Systems).

Protective group (GP) means, hereinafter, a group that is able, on the one hand, to protect a reactive function such as a hydroxyl or an amine during a synthesis and, on the other hand, to regenerate the reactive function intact at the end of synthesis. Examples of protective groups as well as methods of protection and deprotection are given in "Protective Groups in Organic Synthesis", Greene et al., 3rd Edition (John Wiley & Sons, Inc., New York).

Leaving group (Lg, E, V, X, Z) means, hereinafter, a group that can be easily cleaved from a molecule by rupture of a heterolytic bond, with departure of an electron pair. This group can thus be replaced easily with another group during a substitution reaction, for example. Said leaving groups are, for example, halogens or an activated hydroxyl group such as a mesyl, tosyl, triflate, acetyl, paranitrophenyl, etc. Examples of leaving groups as well as methods of preparation thereof are given in "Advanced Organic Chemistry", J. March, 3rd Edition, Wiley Interscience, p. 310-316.

According to the invention, the compounds of general formula (I) can be prepared according to the methods presented below.

Scheme 1 (Method No. 1):

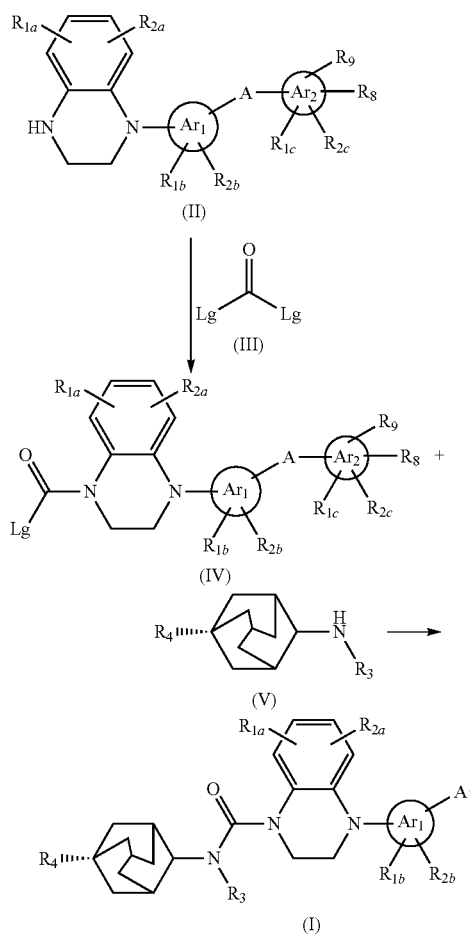

In scheme 1, the compounds of formula (IV) can be prepared by reaction between the intermediates of formula (II) and a carbonyl of formula (III) having two leaving groups Lg (for example a chlorine atom, a trichloromethoxy group, a para-nitrophenyl group, an imidazole group or methyl-imidazolium) in the presence of a base such as triethylamine or diisopropylamine, in a solvent such as dichlomethane or tetrahydrofuran and at a temperature in the range from room temperature to 80° C. The compounds of formula (I) are then obtained by coupling between the activated derivatives (IV) and the amines (V) in the presence or absence of a base such as triethylamine or potassium carbonate, in a solvent such as tetrahydrofuran, dichloromethane, acetonitrile, dimethylformamide or water, at a temperature in the range from room temperature to 100° C.

In certain cases, when $R_1$ or $R_2$ is an alcohol, or $R_1$, $R_2$ or $R_4$ is a primary or secondary amine or an acid or a bioisostere of an acid function (tetrazole, etc.) or if $Ar_1$ or $Ar_2$ has in compound (I) a secondary amine function, it is then necessary to carry out Method No. 1 with a derivative (II) or (V) where the aforementioned functions are made unreactive by the presence of a protective group (for example, for an amine: a Boc, Bn or CBz group; for an alcohol: a Bn group; for an acid: an ester group; for a tetrazole: a benzyl group). Finally, to obtain the desired functionality, it is then necessary to carry out a reaction of deprotection in conditions known by person skilled in the art.

The heterocycles of general formula (V) are available commercially or can be prepared by methods described in the literature (for example WO 2007/077949, US 2005/0215784 A1, US 2005/0245745 A1, Journal of Organic Chemistry (2005), 70(20), 7919-7924).

Scheme 2 gives the details of a synthesis of the compounds of formula (II).

Scheme 2:

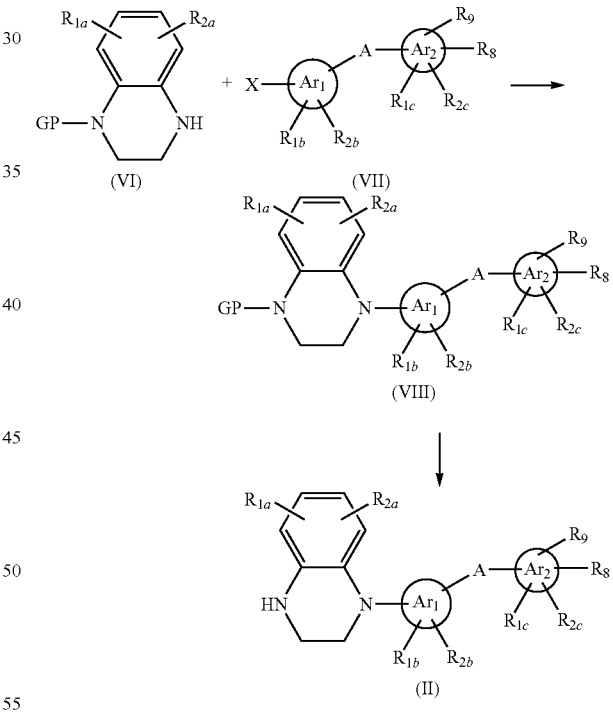

In scheme 2, the compounds of formula (VIII) can be prepared by coupling between a monoprotected tetrahydroquinoxaline of formula (VI) and a derivative (VII) having a leaving group X (for example a halogen, a tosylate, triflate or nanoflate group) in the presence of an organometallic catalyst such as a palladium derivative, in the presence or absence of a phosphine such as tritertbutylphosphine or triphenylphosphine, in the presence of a base such as potassium carbonate, potassium fluoride, potassium tertbutylate or potassium phosphate in a solvent or mixture of solvents such as dioxane, ethylene glycol dimethyl ether, toluene, tetrahydrofuran or water, at a temperature in the range from room temperature to 100° C. The amines (II) are obtained by deprotection of the amine function of the compounds of formula (VIII), by methods selected from those known by a person skilled in the art; they comprise among others the use of trifluoroacetic acid or hydrochloric acid in dichloromethane, dioxane, tetrahydrofuran or diethyl ether in the case of protection by a Boc group, and piperidine for an Fmoc group, at temperatures in the range from −10 to 100° C.

The heterocycles of general formula (VI) are available commercially or can be prepared by methods described in the literature (for example "Comprehensive heterocyclic chemistry", Katritzky et al., 2nd Edition (Pergamon Press); Krchnak, V. et al., Tet. Lett (2001), 42, 2443-2446; Eary, C. T. et al., Tet. Lett. (2006), 47, 6899-6902; Savrides, E-M. et al., J. Het. Chem. (2005), 42, 1031-1034. De Selms, R. C. et al., J. Het. Chem. (1974), 11(4), 595-7.

The compounds of general formula (VII) are available commercially or can be prepared by methods described in the literature (for example Z. Sui et al., Bioorg. Med. Chem. Lett. (2003), 13, 761-765; Chopa, A. B. et al., J. Organomet. Chem. (2005), 690(17), 3865-3877; Düggeli, M. et al., Org. Biomol. Chem. (2003), 1(11), 1894-1899; Gros, P. et al., J. Org. Chem (2003), 68(5), 2028-2029; Bouillon, A. et al., Tet. (2002), 58(14), 2885-2890; Balle, T. et al., J. Med. Chem. (2006), 49(11), 3159-3171; M. A. Ismail et al., J. Med. Chem. (2006), 49(17), 5324-5332, Gu, Y. G. et al., J. Med. Chem. (2006), 49(13), 3770-3773; Serafin, B. et al., Eur. J. Med. Chem. (1977), 12(4), 325-31; Schmidt, H-W. et al., J. Het. Chem. (1987), 24(5), 1305-7; Walsh, D. A. et al., J. Med. Chem. (1990), 33(7), 2028-32; WO 2005/042521; EP 0 277 725).

Scheme 3 gives the details of a synthesis of the compounds of formula (VIII) in which $Ar_1$ represents a pyridine nucleus (Y=C) or pyrimidine nucleus (Y=N); these compounds will be called compounds of formula (IX) hereinafter.

Scheme 3:

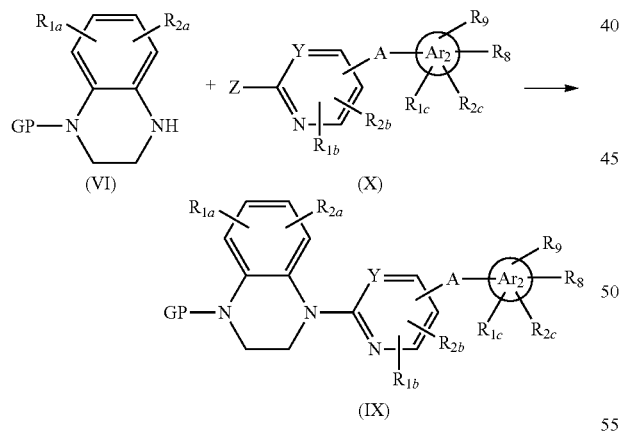

In scheme 3, the compounds of formula (IX) can be prepared by a reaction of nucleophilic aromatic substitution between a monoprotected tetrahydroquinoxaline of formula (VI) and a derivative (X) having a leaving group Z (for example a halogen or an alkylsulfonyl group) in the presence of a base such as the lithium salt of hexamethyldisilazane or sodium hydride in a solvent such as tetrahydrofuran, N-methylpyrrolidinone, dimethylsulfoxide or dimethylformamide, at a temperature from room temperature to 100° C.

Scheme 4 gives the details of a synthesis of the compounds of formula (VIII) in which $Ar_1$ represents a phenyl nucleus and A represents a bond; these compounds will be called compounds of formula (XI) hereinafter.

Scheme 4:

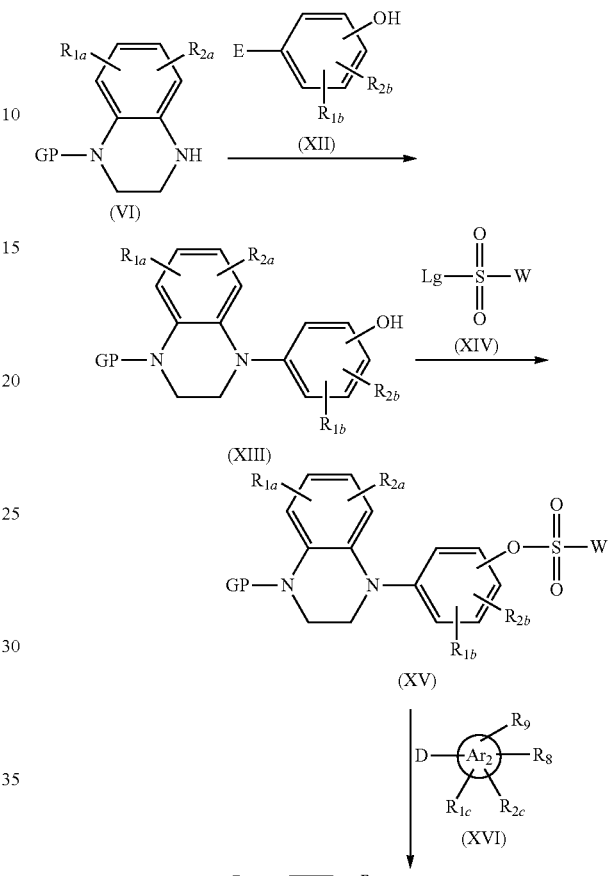

In scheme 4, the compounds of formula (XIII) can be prepared by a coupling reaction between a monoprotected tetrahydroquinoxaline of formula (VI) and a derivative (XII) having a leaving group E (for example a halogen, triflate or nanoflate) in the presence of an organometallic catalyst such as a palladium derivative, in the presence or absence of a phosphine such as tritertbutylphosphine or triphenylphosphine, in the presence of a base such as potassium or cesium carbonate, potassium fluoride, potassium tertbutylate or potassium phosphate in a solvent or mixture of solvents such as dioxane, ethylene glycol dimethyl ether, toluene, tetrahydrofuran or water, at a temperature in the range from room temperature to 100° C. The phenol function is then converted to a sulfonic ester to form the compounds (XV) by the action of a sulfonic derivative (XIV), where $SO_2W$ represents for example a mesylate, tosylate, triflate or nanoflate group, such as a sulfonic anhydride (Lg=$OSO_2W$), a sulfonic acid fluoride (Lg=F) or a sulfonic acid chloride (Lg=Cl), in the presence of a base or of a mixture of bases such as triethylamine, pyridine, dimethylaminopyridine, diisopropylethylamine or potassium carbonate in a solvent or mixture of solvents such as dichloromethane, chloroform, toluene, tetrahydrofuran, dimethylformamide or acetonitrile, at a temperature in the range from −78° C. to 100° C. Finally, the derivatives (XI) can be obtained by a coupling reaction between a derivative (XV) and a compound (XVI) in which D represents an organometallic group (for example a derivative of boron, a derivative of tin or an organozinc compound) in the presence of an organometallic species such as a palladium derivative, in the presence or absence of a phosphine such as tricyclohexylphosphine or triphenylphosphine, in the presence of a base such as potassium carbonate or potassium fluoride in a solvent or mixture of solvents such as dioxane, dimethylformamide, ethylene glycol dimethyl ether, tetrahydrofuran or water, at a temperature in the range from room temperature to 100° C.

Scheme 5 presents an alternative synthesis of the compounds of formula (XI).

the derivatives (XI) can be obtained by a coupling reaction between the derivative (XVII) and a compound (XVIII) having a leaving group V (for example a halogen, a triflate, a nonaflate) in the presence of an organometallic catalyst such as a palladium derivative, in the presence or absence of a phosphine such as tricyclohexylphosphine or triphenylphosphine, in the presence of a base such as sodium or potassium carbonate or potassium fluoride, in a solvent or mixture of solvents such as dioxane, dimethylformamide, ethylene glycol dimethyl ether, tetrahydrofuran or water, at a temperature in the range from room temperature to 100° C.

Scheme 6 gives the details of a synthesis of the compounds of formula (VIII) in which $Ar_1$ represents a pyridine nucleus (just one of the two atoms Y is a nitrogen, the other is a carbon) and A represents a bond; these compounds will be called compounds of formula (XIX) hereinafter.

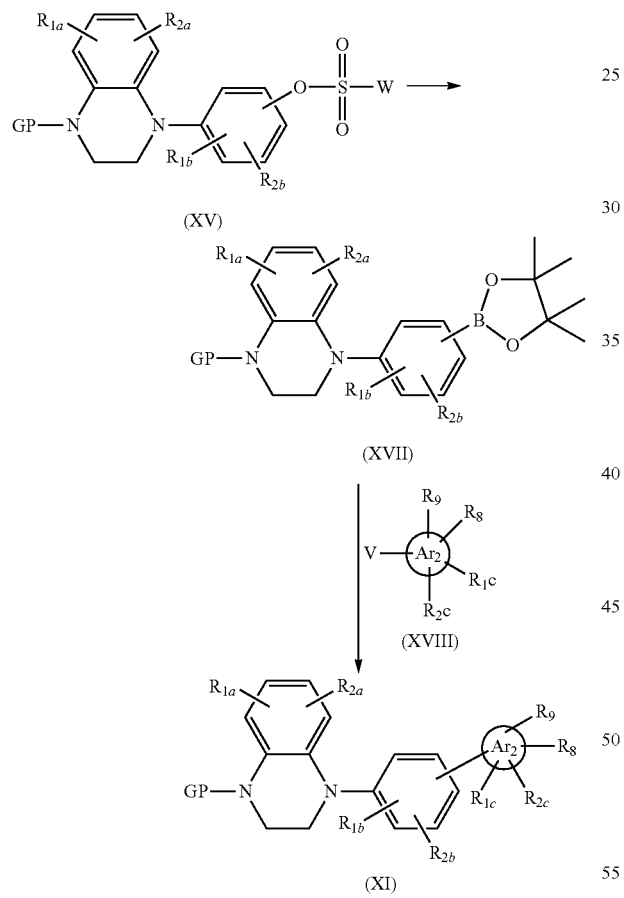

Scheme 5:

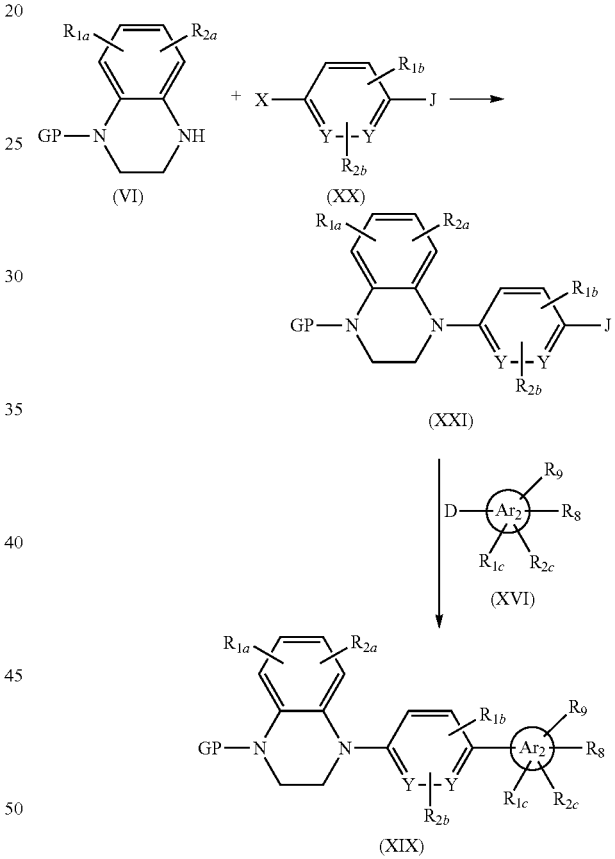

Scheme 6:

In scheme 5, the compounds of formula (XVII) can be prepared by transformation of the sulfonic ester function of the compounds (XV) to a boronic ester function to obtain the compounds (XVII) by a reaction with bispinacolatodiborane in the presence of a palladium complex such as 1,1'-bis(diphenylphosphino)ferrocedichloropalladium (II) in the presence of a base such as potassium acetate and lithium chloride in a solvent or mixture of solvents such as dichloromethane, dioxane or dimethylsulfoxide, at a temperature in the range from room temperature to 100° C. In a second step, In scheme 6, the compounds of formula (XXI) can be prepared by a reaction of aliphatic or aromatic nucleophilic substitution between a monoprotected tetrahydroquinoxaline of formula (VI) and a derivative (XX) having a leaving group X (for example a fluorine atom) and a leaving group J (for example a bromine atom) in the presence of a base such as potassium tertbutylate or sodium hydride in a solvent such as N-methylpyrrolidinone or dimethylformamide, at a temperature in the range from room temperature to 100° C. Finally, the derivatives (XIX) can be obtained by a coupling reaction between a derivative (XXI) and a compound (XVI) in which D is either an organometallic group (for example a derivative of boron, a derivative of tin or an organozinc compound) or a hydrogen atom when it is joined directly to the nitrogen atom of an amine of a heterocycloalkyl, in the presence of an organometallic catalyst such as a palladium derivative, in the presence or absence of a phosphine such as tricyclohexylphosphine or triphenylphosphine, in the presence of a base such as potassium or cesium carbonate, potassium triphosphate, sodium or potassium tert-butylate, or potassium fluoride, in a solvent or mixture of solvents such as toluene, dioxane, dimethylformamide, ethylene glycol dimethyl ether, tetrahydrofuran or water, at a temperature in the range from room temperature to 100° C.

Scheme 7 gives the details of a synthesis of the compounds of formula (VIII) in which $Ar_2$ is a piperazine group, A is a single bond joined directly to one of the two nitrogen atoms of the piperazine, $R_{1c}$ is joined to the other nitrogen atom of the piperazine; these compounds will be called compounds of formula (XXII) hereinafter.

Scheme 7:

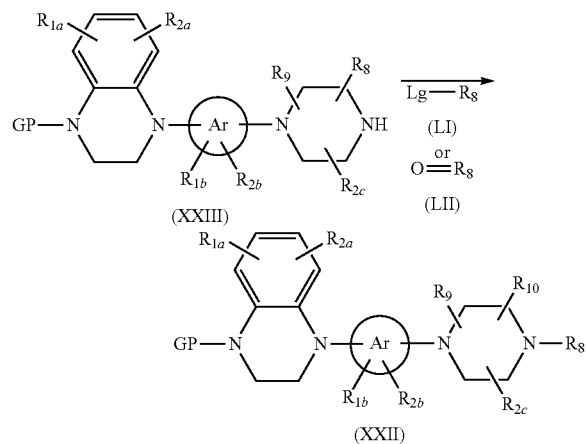

The compounds (XXII) can be obtained following various reactions:
- A derivative (LI) of the sulfonyl chloride, acid chloride or carbamoyl chloride type (Lg is then a chlorine atom) can be reacted with the compound (XXIII), in the presence of a base such as triethylamine, diisopropylethylamine or pyridine, with or without solvent such as dichloromethane, chloroform, tetrahydrofuran or dioxane at a temperature in the range from 0 to 40° C.
- An alkylation reaction is also possible between the compound (XXIII) and a derivative (LI) in which Lg is for example a chlorine, bromine or iodine atom, a tosylate or triflate group, in the presence of a base such as triethylamine, diisopropylethylamine, in a solvent such as tetrahydrofuran or dioxane at a temperature in the range from 0 to 80° C.
- A reductive amination reaction can also be carried out between the compound (XXIII) and a derivative (LII) of the aldehyde or ketone type, using a reducing agent such as sodium borohydride, sodium triacetoxyborohydride or sodium cyanoborohydride, in the presence or absence of a Brønsted acid (such as hydrochloric acid) or a Lewis acid (such as titanium tetraisopropoxide) in a solvent such as dichloroethane, dichloromethane, acetic acid or methanol, at temperatures between −10° C. and 30° C.

Scheme 8 gives the details of a synthesis of the compounds of formula (I) in which $Ar_2$ is a piperidine group, A is a single bond joined directly to the nitrogen of the piperidine, $R_8$ is a heterocycloalkyl which is joined in position 4 of the nitrogen atom of the piperidine; these compounds will be called compounds of formula (XXXVI) hereinafter.

Scheme 8 (Method No. 2):

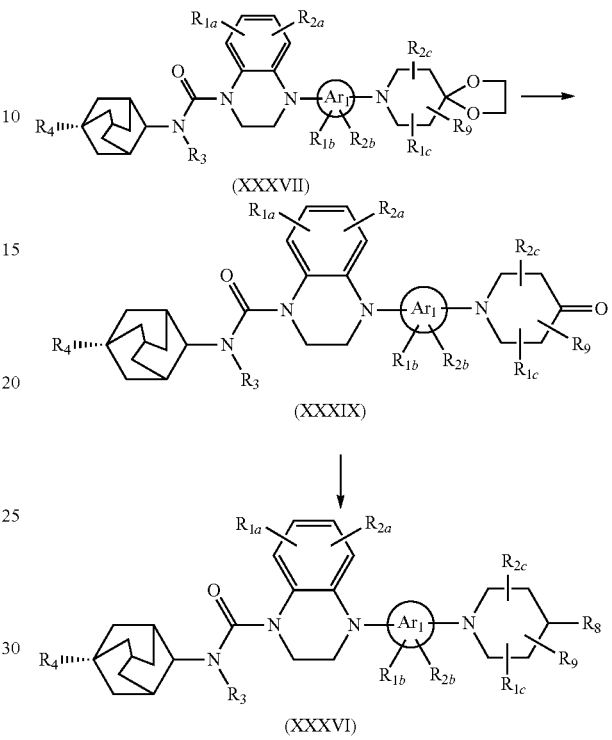

In scheme 8, the derivatives (XXXIX) are obtained by hydrolysis of the cyclic acetal function of the compound (XXXVII) by means of an acid such as hydrochloric acid in a solvent or mixture of solvents such as water, an alcohol, dioxane at a temperature in the range from room temperature to 100° C., leading to the ketones (XXXIX). The last step consists of a reaction of reductive amination which can be performed between the compound (XIX) and a heterocycle having an amine function, using a reducing agent such as sodium borohydride, sodium triacetoxyborohydride or sodium cyanoborohydride, in the presence or absence of a Brønsted acid (such as hydrochloric acid) or a Lewis acid (such as titanium tetraisopropoxide) in a solvent such as dichloroethane, dichloromethane, acetic acid or methanol, at temperatures between −10° C. and 30° C.

Scheme 9 gives the details of a synthesis of the compounds of formula (XVI) in which $Ar_2$ is a piperidine group, $R_8$ and $R_9$ are joined in position 4 of the nitrogen atom of the piperidine and forms a halocyclopropyl spiro group; these compounds will be called compounds of formula (XXXX) hereinafter.

Scheme 9:

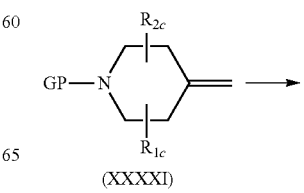

-continued

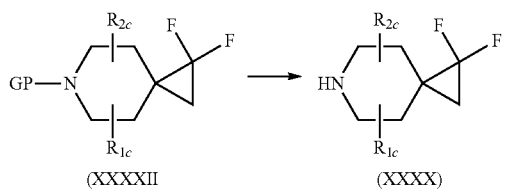

In scheme 9, the difluorocyclopropane derivatives (XXXXII) are obtained by cyclopropanation of the double bond of the compounds (XXXXI) by means of trimethylsilyl 2-(fluorosulfonyl)difluoroacetate in the presence of a source of fluoride ions such as NaF optionally in a solvent such as xylene at a temperature in the range from room temperature to 150° C. The amines (XXXX) are obtained by deprotection of the amine function of the compounds of formula (XXXXII), by methods selected from those known by a person skilled in the art; they comprise among others the use of trifluoroacetic acid or of hydrochloric acid in dichloromethane, dioxane, tetrahydrofuran or diethyl ether in the case of protection by a Boc group, and of piperidine for an Fmoc group, at temperatures in the range from −10 to 100° C.

Scheme 10 gives the details of a synthesis of the compounds of formula (XVI) in which $Ar_2$ is a piperidine group, $R_8$ is joined in position 4 of the nitrogen atom of the piperidine and represents an alkoxy-imino function; these compounds will be called compounds of formula (XXIII) hereinafter.

Scheme 10:

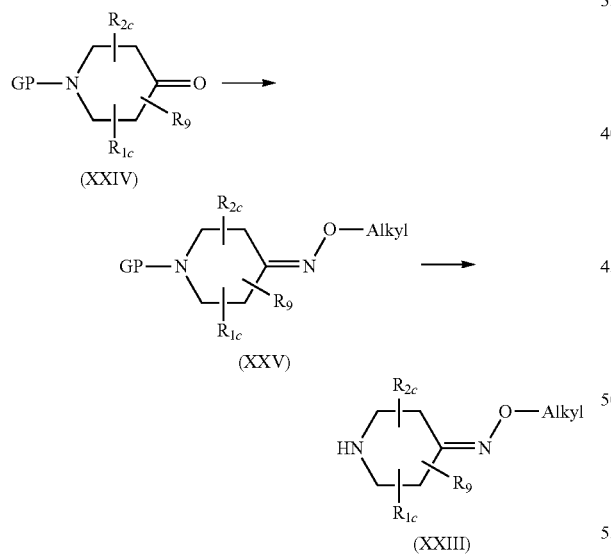

In scheme 10, the oximes (XXV) are obtained by transformation of the ketone of the compounds (XXIV) by means of O-alkylhydroxyamine in the form of base or of hydrochloride in the presence or absence of a base such as sodium acetate or triethylamine in a solvent such as methanol or ethanol at a temperature from 0° C. to room temperature. The amines (XXIII) are obtained by deprotection of the amine function of the compounds of formula (XXV), by methods selected from those known by a person skilled in the art; they comprise among others the use of trifluoroacetic acid or hydrochloric acid in dichloromethane, dioxane, tetrahydrofuran or diethyl ether in the case of protection by a Boc group, and of piperidine for an Fmoc group, at temperatures in the range from −10 to 100° C.

Scheme 11 gives the details of a synthesis of the compounds of formula (VIII) in which $Ar_2$ represents a piperidine nucleus bound to $Ar_1$ by the nitrogen atom and in which $R_8$ and $R_9$ are joined in position 4 of the nitrogen atom of the piperidine and forms together a cyclopropyl spiro group substituted with an alkyl ester function and A represents a bond; these compounds will be called compounds of formula (XXVI) hereinafter.

Scheme 11:

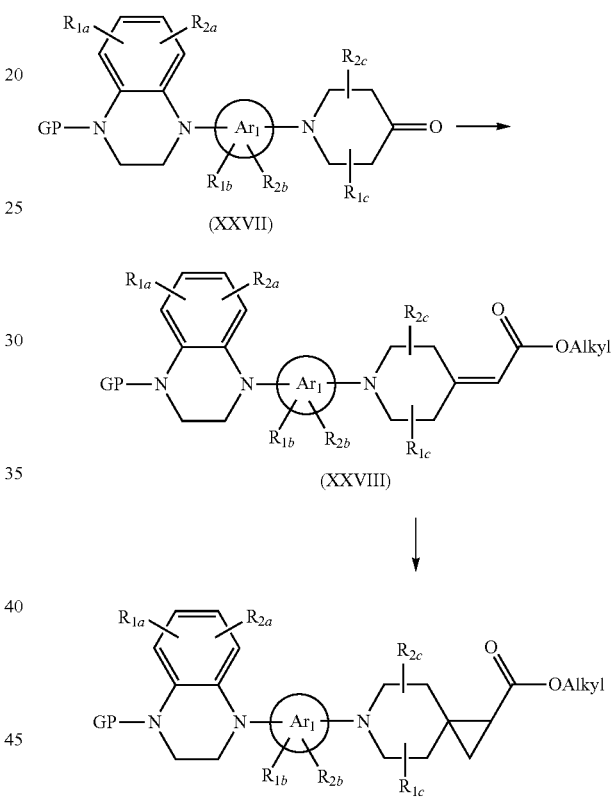

In scheme 11, the derivatives (XXVIII) are obtained by transformation of the ketone of the compounds (XXVII) by means of a Wittig-Horner reaction using for example a phosphonate ylide such as diethyl((ethoxycarbonyl)methyl)phosphonate in the presence of a base such as NaH or tBuOK in a solvent such as THF or DMSO at a temperature in the range from 0° C. to room temperature. Finally, the compounds (XXVI) are obtained by cyclopropanation of the ethylene derivatives (XXVIII) by means of a reaction of cyclopropanation of the Corey-Chaykovsky type using for example trimethylsulfoxonium iodide in the presence of a base such as NaH or tBuOK in a solvent such as DMSO.

Scheme 12 gives the details of a synthesis of the compounds of formula (XVI) in which $Ar_2$ is a [1,4]azasilinane group, $R_{1c}$ and $R_{2c}$ are hydrogen atoms, $R_8$ and $R_9$ are joined to the silicon atom; these compounds will be called compounds of formula (XXIX) hereinafter.

Scheme 12:

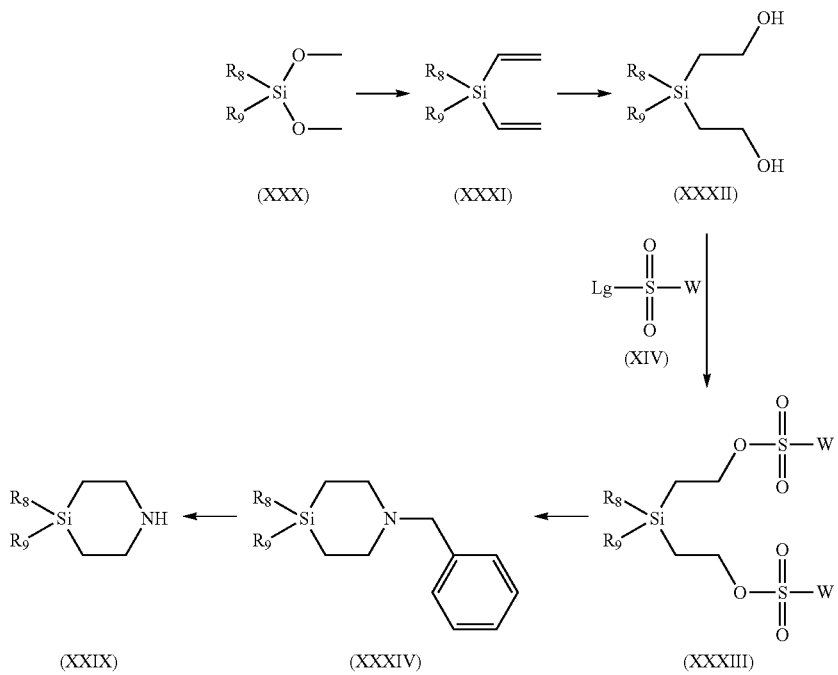

In scheme 12, the derivatives (XXXI) are obtained by addition of an organometallic derivative such as vinylmagnesium to the compounds (XXX) in a solvent such as THF or ether at a temperature in the range from room temperature to 80° C. The following reaction is a hydroboration of the double bonds of the derivatives (XXXI) to form the alcohols (XXXII) by means of a boron derivative such as 9-BBN or $BH_3$, then oxidation in an alkaline medium for example with a mixture of $H_2O_2$ and soda. Then the two hydroxyl functions of the compounds (XXXII) are converted to a sulfonic ester function to form the compounds (XXXIII) by the action of a sulfonic derivative (XIV) where $SO_2W$ represents for example a mesylate, tosylate, triflate or nanoflate group, such as a sulfonic anhydride (Lg=$OSO_2W$), a sulfonic acid fluoride (Lg=F) or a sulfonic acid chloride (Lg=Cl), in the presence of a base or of a mixture of bases such as triethylamine, pyridine, dimethylaminopyridine, diisopropylethylamine or potassium carbonate in a solvent or mixture of solvents such as dichloromethane, chloroform, toluene, tetrahydrofuran, dimethylformamide or acetonitrile, at a temperature in the range from −78° C. to 100° C. The following reaction, which can be carried out at the same time as the preceding step, is nucleophilic substitution of the two sulfonic ester functions of the compounds (XXXIII) by benzylamine, leading to the heterocycles (XXXIV). The derivatives (XXIX) are finally obtained by elimination of the benzyl group borne by the amino group of the compounds (XXXIV). The possible methods of deprotection comprise, among others, the use of hydrogen in the presence of a catalyst derived from palladium for performing a reaction of hydrogenolysis, in a solvent or mixture of solvents such as methanol, ethanol, ethyl acetate, tetrahydrofuran, under a hydrogen pressure between 1 and 10 bar at a temperature in the range from room temperature to 80° C. An alternative method for performing the elimination of the benzyl group from a secondary amine consists of applying the Olofson reaction (as described in Tett. Lett. 1977, page 1570, and J. Org. Chem. 1990, 55, page 1) in which a chloroformate is used, such as vinyl or chloroethyl chloroformate, which can lead to the heterocycles (XXIX) in the form of hydrochloride, with or without treatment with an aqueous solution of HCl.

In the schemes presented above, the starting compounds and the reagents, when their manner of preparation is not described, are commercially available or are described in the literature, or else can be prepared according to methods that are described in the literature or that are known by a person skilled in the art.

The invention, according to another of its aspects, also relates to the compounds of formulas (II), (IV), (VIII), (X), (XI), (XIII), (XV), (XVI), (XVII), (XXI), (XIX), (XXII), (XXVIII), (XXXVII), (XXXVI), etc. defined above. These compounds are useful as intermediates for synthesis of the compounds of formula (I).

The following abbreviations and empirical formulas are used:

| | |
|---|---|
| 9-BBN | 9-borabicyclo[3.3.1]nonane |
| ° C. | degree Celsius |
| DME | dimethoxyethane |
| DMF | dimethylformamide |
| DMSO | dimethyl sulfoxide |
| h | hour(s) |
| $H_2$ | dihydrogen |
| $H_2O$ | water |
| HCl | hydrochloric acid |
| $K_2CO_3$ | potassium carbonate |
| LC/MS | liquid chromatography/mass spectrometry |
| ml or mL | milliliter(s) |
| mmol | millimole(s) |
| MHz | MegaHertz |
| $MgSO_4$ | magnesium sulfate |
| N | normal |

| | |
|---|---|
| NMP | N-methylmorpholine |
| NaHCO$_3$ | sodium hydrogen carbonate |
| Pd/C | palladium on charcoal |
| P$_2$O$_5$ | phosphorus pentoxide |
| ppm | parts per million |
| psi | pounds per square inch |
| SO$_2$ | sulfur dioxide |

Example 1

Trans 4-(4-tert-butoxyimino-3,4,5,6-tetrahydro-2H-[1,3']bipyridinyl-6'-yl)-3,4-dihydro-2H-quinoxaline-1-carboxylic acid (5-hydroxy-adamantan-2-yl)-amide (Trans (5-hydroxy-adamantan-2-yl)-amide of 4-(4-tert-butoxyimino-3,4,5,6-tetrahydro-2H-[1,3']bipyridinyl-6'-yl)-3,4-dihydro-2H-quinoxaline-1-carboxylic acid) (compound No. 2)

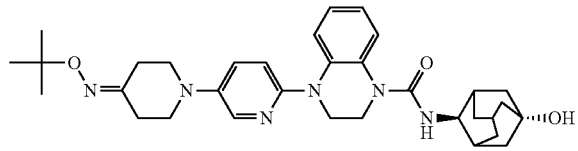 [SMILES: CC(C)(C)ON=C1CCN(c2ccc(N3CCN(C(=O)N[C@H]4C5CC6CC4C[C@@](O)(C6)C5)c4ccccc43)nc2)CC1]

1.1: tert-Butyl Ester of 4-(5-bromo-pyridin-2-yl)-3,4-dihydro-2H-quinoxaline-1-carboxylic acid 30 g of tert-butyl ester of 3,4-dihydro-2H-quinoxaline-1-carboxylic acid is put in 430 ml of N-methyl pyrrolidinone at 0° C. under nitrogen. 30 g of potassium tert-butylate is added a little at a time, keeping the temperature below 10° C. It is stirred for 1.5 h at room temperature, then 850 ml of water and 800 ml of ethyl ether are added at 0° C. The aqueous phase is extracted with 800 ml of ethyl ether, then with 400 ml of ethyl ether. The organic phases are combined and then dried over magnesium sulfate and concentrated to dryness. Then 300 ml of pentane is added to the raw reaction product and the heterogeneous mixture obtained is sonicated with ultrasound for 5 min. The mixture is then held at 5° C. for 48 h, then the solid is filtered, washed three times with pentane and then dried at 40° C. for 5 h. 35 g of tert-butyl ester of 4-(5-bromo-pyridin-2-yl)-3,4-dihydro-2H-quinoxaline-1-carboxylic acid is obtained.
M+H$^+$=392.0

1.2: tert-Butyl ester of 4-tert-butoxyimino-piperidine-1-carboxylic acid 0.662 g of O-tert-butylhydroxylamine hydrochloride is put in a flask of suitable size and 12 ml of ethanol is added, and then 0.432 g of sodium acetate. The reaction mixture is then refluxed for 15 minutes, then 1 g of tert-butyl ester of 4-oxo-piperidine-1-carboxylic acid, previously dissolved in 13 ml of ethanol, is added. After heating for 1.5 h, the reaction mixture is cooled to room temperature and the ethanol is evaporated under reduced pressure. The residue is taken up in dichloromethane, dried over sodium sulfate, filtered, concentrated to dryness and dried under vacuum. 1.32 g of tert-butyl ester of 4-tert-butoxyimino-piperidine-1-carboxylic acid (97%) is obtained in the form of a white solid.
(M+H$^+$)=271

1.3: Piperidin-4-one O-tert-butyl-oxime

A solution of 34 ml of dichloromethane containing 0.9 g of tert-butyl ester of 4-tert-butoxyimino-piperidine-1-carboxylic acid is cooled to 0° C. 25 ml of a 4M solution of hydrochloric acid in dioxane (30 eq) is added. The reaction mixture is stirred at room temperature for 3 hours and then diluted by adding dichloromethane. A saturated solution of sodium hydrogen carbonate is then added until pH=8 is obtained. The aqueous phase is extracted three times with dichloromethane. The organic phases are then combined, dried over sodium sulfate, filtered and concentrated to dryness under reduced pressure. 0.49 g of piperidin-4-one O-tert-butyl-oxime is obtained.
(M+H$^+$)=171

1.4: tert-Butyl ester of 4-(4-tert-butoxyimino-3,4,5,6-tetrahydro-2H-[1,3']bipyridinyl-6'-yl)-3,4-dihydro-2H-quinoxaline-1-carboxylic acid 0.229 g of piperidin-4-one O-tert-butyl-oxime, 0.172 g of sodium tert-butylate, 0.084 g of dicyclohexyl-(2',6'-dimethoxy-biphenyl-2-yl)-phosphane and 0.047 g of tris(dibenzylideneacetone)dipalladium (0) are added to a solution of 8 mL of anhydrous toluene containing 0.5 g of tert-butyl ester of 4-(5-bromo-pyridin-2-yl)-3,4-dihydro-2H-quinoxaline-1-carboxylic acid (intermediate 1.1). The reaction mixture is heated to 115° C. After heating for 2 h, the solution is cooled to room temperature and then filtered on Celite. The solvents are evaporated under reduced pressure. The residue is taken up in ethyl acetate. The organic phase is then washed with water, dried over sodium sulfate, filtered and concentrated to dryness under reduced pressure. The residue obtained is purified by silica column chromatography, eluting with a gradient of a dichloromethane/methanol mixture (95/5 to 60/40), and 0.526 g of tert-butyl ester of 4-(4-tert-butoxyimino-3,4,5,6-tetrahydro-2H-[1,3']bipyridinyl-6'-yl)-3,4-dihydro-2H-quinoxaline-1-carboxylic acid is obtained.
(M+H$^+$)=480

1.5. 6'-(3,4-Dihydro-2H-quinoxalin-1-yl)-2,3,5,6-tetrahydro-[1,3']bipyridinyl-4-one O-tert-butyl-oxime A solution of 11 mL of dichloromethane containing 0.526 g of tert-butyl ester of 4-(4-tert-butoxyimino-3,4,5,6-tetrahydro-2H-[1,3']bipyridinyl-6'-yl)-3,4-dihydro-2H-quinoxaline-1-carboxylic acid is cooled to 0° C. 3.6 ml of a 4M solution of hydrochloric acid in dioxane is added. The reaction mixture is stirred while cold for 3 hours and then is diluted with dichloromethane. Then water is added, and then sodium carbonate until pH=12 is obtained. The aqueous phase is extracted three times with dichloromethane. The organic phases are then combined, dried over sodium sulfate, filtered and concentrated to dryness under reduced pressure. 0.485 g of 6'-(3,4-dihydro-2H-quinoxalin-1-yl)-2,3,5,6-tetrahydro-[1,3']bipyridinyl-4-one O-tert-butyl-oxime is obtained.
(M+H$^+$)=380

1.6: trans-(5-Hydroxy-adamantan-2-yl)-amide of 4-(4-tert-butoxyimino-3,4,5,6-tetrahydro-2H-[1,3']bipyridinyl-6'-yl)-3,4-dihydro-2H-quinoxaline-1-carboxylic acid A solution under nitrogen of 13 ml of anhydrous dichloromethane containing 0.485 g of 6'-(3,4-dihydro-2H-quinoxalin-1-yl)-2,3,5,6-tetrahydro-[1,3']bipyridinyl-4-one O-tert-butyl-oxime and 0.35 mL of triethylamine is cooled to 0° C. 0.151 g of triphosgene is then added. After stirring for 2 hours at room temperature, 1 g of trans-4-amino-adamantan-1-ol alcohol, 0.36 ml of triethylamine (2 eq) and 1 ml of anhydrous dimethylformamide are added. Stirring is maintained for 18 hours. The solvents are evaporated under reduced pressure and the residue is taken up in water, then a solution of sodium carbonate is added until basic pH is obtained. The aqueous phase is extracted three times with dichloromethane. The organic phases are then combined, dried over sodium sulfate, filtered and concentrated to dryness under reduced pressure. The residue obtained is purified by silica column chromatography, eluting with a gradient of a dichloromethane/methanol mixture (95/5 to 0/100). 0.428 g of trans-(5-hydroxy-adamantan-2-yl)-amide of 4-(4-tert-butoxyimino-3,4,5,6-tetrahydro-2H-[1,3']bipyridinyl-6'-yl)-3,4-dihydro-2H-quinoxaline-1-carboxylic acid is obtained.

(M+H$^+$)=573, MP=110-113° C.;

$^1$H NMR (400 MHz, DMSO-d6) δ(ppm)=8.07 (d, J=3 Hz, 1H), 7.44 (dd, J=7.9 Hz and 1.5 Hz, 1H), 7.40 (dd, J=9 Hz and 3 Hz, 1H), 7.11 (m, 2H), 6.94 (m, 1H), 6.86 (m, 1H), 6.00 (d, J=6 Hz, 1H), 4.38 (s, 1H), 3.79 (m, 4H), 3.70 (m, 1H), 3.33 (m, 2H), 3.27 (m, 2H), 2.61 (m, 2H), 2.41 (m, 2H), 2.04 (m, 2H), 1.99 (m, 1H), 1.73 to 1.57 (m, 8H), 1.36 (m, 2H), 1.25 (s, 9H).

Example 2

Trans 4-{5-[4-(2,2-difluoro-cyclopropylmethyl)-piperazin-1-yl]-pyridin-2-yl}-3,4-dihydro-2H-quinoxaline-1-carboxylic acid (5-carbamoyl-adamantan-2-yl)-amide; (trans-(5-Carbamoyl-adamantan-2-yl)-amide of 4-{5-[4-(2,2-difluoro-cyclopropylmethyl)-piperazin-1-yl]-pyridin-2-yl}-3,4-dihydro-2H-quinoxaline-1-carboxylic acid) (compound No. 4)

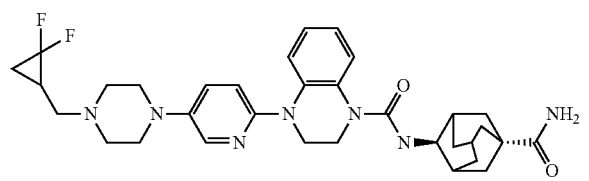 [SMILES: NC(=O)[C@]12CC3CC(C1)[C@H](NC(=O)N1CCN(c4ccc(N5CCN(CC6CC6(F)F)CC5)cn4)c4ccccc41)C(C3)C2]

2.1: tert-Butyl ester of 4-[5-(4-benzyloxycarbonyl-piperazin-1-yl)-pyridin-2-yl]-3,4-dihydro-2H-quinoxaline-1-carboxylic acid 10.12 g of tert-butyl ester of 4-(5-bromo-pyridin-2-yl)-3,4-dihydro-2H-quinoxaline-1-carboxylic acid (intermediate 1.1) and 5.7 g of 4-carboxybenzyl piperazine are mixed in 118 ml of toluene, then 0.95 g of tris(dibenzylideneacetone)dipalladium (0), 1.7 g of 2-dicyclohexylphosphino-2',6'-dimethoxybiphenyl and 3.5 g of sodium tert-butylate are added. The reaction mixture is heated at 110° C. for 3 h. Then ethyl acetate is added and the mixture is washed once with water and once with a saturated aqueous solution of sodium chloride. The organic phase is dried over magnesium sulfate and concentrated under reduced pressure. The raw product obtained is chromatographed on silica gel, eluting with a gradient of a mixture of heptane/ethyl acetate (90/10 to 0/100). 10.16 g of tert-butyl ester of 4-[5-(4-benzyloxycarbonyl-piperazin-1-yl)-pyridin-2-yl]-3,4-dihydro-2H-quinoxaline-1-carboxylic acid is obtained.

M+H$^{+=530.5}$ 2.2: tert-Butyl ester of 4-(5-piperazin-1-yl-pyridin-2-yl)-3,4-dihydro-2H-quinoxaline-1-carboxylic acid 5.08 g of tert-butyl ester of 4-[5-(4-benzyloxycarbonyl-piperazin-1-yl)-pyridin-2-yl]-3,4-dihydro-2H-quinoxaline-1-carboxylic acid in 240 ml of ethanol is put in a Parr bottle, then 2 g of Pd/C 10% (50% in water) is added. The resultant reaction mixture is stirred at 35° C. under 45 psi of hydrogen for 3.5 h. Then it is filtered under inert atmosphere on a Whatman filter and then rinsed several times with methanol, which is then evaporated under reduced pressure. 3.57 g of tert-butyl ester of 4-(5-piperazin-1-yl-pyridin-2-yl)-3,4-dihydro-2H-quinoxaline-1-carboxylic acid is obtained.

M+H$^{+=396.6}$ 2.3: tert-Butyl ester of 4-{5-[4-(2,2-difluoro-cyclopropylmethyl)-piperazin-1-yl]-pyridin-2-yl}-3,4-dihydro-2H-quinoxaline-1-carboxylic acid 0.3 g of tert-butyl ester of 4-(5-piperazin-1-yl-pyridin-2-yl)-3,4-dihydro-2H-quinoxaline-1-carboxylic acid is added to 10 mL of acetonitrile, to which 0.189 g of K$_2$CO$_3$ and then 10.143 g of 2-bromomethyl-1,1-difluoro-cyclopropane are added. The reaction mixture is stirred for 2 h at room temperature under nitrogen, then for 18 h under reflux under nitrogen. The reaction mixture is then cooled to room temperature, poured into 100 mL of H$_2$O and extracted 3 times with 50 ml of EtOAc. The resultant organic phases are combined, washed with 100 ml of H$_2$O, 100 ml of a saturated aqueous solution of sodium chloride, dried over MgSO$_4$, filtered and concentrated to dryness. The raw product obtained is chromatographed on silica gel, eluting with a gradient of methanol in dichloromethane ranging from 1% to 8%. 0.3 g of tert-butyl ester of 4-{5-[4-(2,2-difluoro-cyclopropylmethyl)-piperazin-1-yl]-pyridin-2-yl}-3,4-dihydro-2H-quinoxaline-1-carboxylic acid is obtained.

[M+H$^+$]=486

2.4: 1-{5-[4-(2,2-Difluoro-cyclopropylmethyl)-piperazin-1-yl]-pyridin-2-yl}-1,2,3,4-tetrahydroquinoxaline 0.3 g of tert-butyl ester of 4-{5-[4-(2,2-difluoro-cyclopropylmethyl)-piperazin-1-yl]-pyridin-2-yl}-3,4-dihydro-2H-quinoxaline-1-carboxylic acid is put in 5 mL of dioxane, to which 2.32 ml of 4N HCl in dioxane is added. The reaction mixture is stirred at room temperature in a closed environment for 18 h. Once again, 2.32 mL of 4N HCl in dioxane is added, and the reaction mixture is stirred for a further 18 h at room temperature. 2.32 ml of 4N HCl in dioxane is added once again, and the reaction mixture is stirred for a further 18 h at room temperature. After concentration to dryness, the reaction mixture is diluted with a solution of 50 ml of 1N HCl in water and extracted with 100 ml of diethyl ether. The organic phase is washed again with 50 ml of 1N HCl in water. The aqueous phases are then combined, basified with K$_2$CO$_3$ in powder form to pH 10, and extracted 3 times with 50 ml of dichloromethane. The resultant organic phases are combined, washed with a saturated aqueous solution of sodium chloride, dried over MgSO$_4$ and concentrated to dryness. 0.24 g of 1-{5-[4-(2,2-difluoro-cyclopropylmethyl)-piperazin-1-yl]-pyridin-2-yl}-1,2,3,4-tetrahydroquinoxaline is obtained.

[M+H$^+$]=386

2.5: trans-(5-Carbamoyl-adamantan-2-yl)-amide of 4-{5-[4-(2,2-difluoro-cyclopropylmethyl)-piperazin-1-yl]-pyridin-2-yl}-3,4-dihydro-2H-quinoxaline-1-carboxylic acid 0.24 g of 1-{5-[4-(2,2-difluoro-cyclopropylmethyl)-piperazin-1-yl]-pyridin-2-yl}-1,2,3,4-tetrahydroquinoxaline is put in 5 mL of dichloromethane at 0° C. 0.17 mL of triethylamine is added, then 0.073 g of triphosgene. The reaction mixture is stirred for 30 min under nitrogen at 0° C., then for 3 hours at room temperature. Then 0.16 g of amide hydrochloride of trans-4-amino-adamantane-1-carboxylic acid, 0.22 mL of triethylamine and 5 mL of DMF are added. The reaction mixture is stirred for 18 h at room temperature under nitrogen. After hydrolysis with 100 ml of $H_2O$, the mixture is extracted twice with 50 ml of dichloromethane. The organic phases are combined, washed twice with 100 ml of $H_2O$, then with 100 ml of a saturated aqueous solution of sodium chloride, dried over $MgSO_4$ and concentrated to dryness. The raw product obtained is chromatographed on silica gel, eluting with a gradient of methanol in dichloromethane ranging from 1% to 10%. After trituration in diethyl ether, filtration and drying, 0.25 g of trans-(5-carbamoyl-adamantan-2-yl)-amide of 4-{5-[4-(2,2-difluoro-cyclopropylmethyl)-piperazin-1-yl]-pyridin-2-yl}-3,4-dihydro-2H-quinoxaline-1-carboxylic acid is obtained.

$[M+H^+]=606$; MP=206° C.;
$^1H$ NMR (400 MHz, DMSO-d6) δ(ppm)=8.05 (d, J=3 Hz, 1H), 7.45 (dd, J=7.9 Hz and 1.5 Hz, 1H), 7.39 (dd, J=9 Hz and 3 Hz, 1H), 7.11 (m, 2H), 6.97 (s.broad, 1H), 6.86 (m, 1H), 6.69 (s.broad, 1H), 6.06 (d, J=6 Hz, 1H), 3.79 (m, 4H), 3.75 (m, 1H), 3.15 (m, 4H), 2.70 to 2.53 (m, 5H), 2.39 (m, 1H), 2.04 to 1.69 (m, 11H), 1.62 (m, 1H), 1.45 (m, 2H), 1.19 (m, 2H).

Example 3

Trans 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide; (trans-(5-carbamoyl-adamantan-2-yl)-amide of 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid) (compound No. 5)

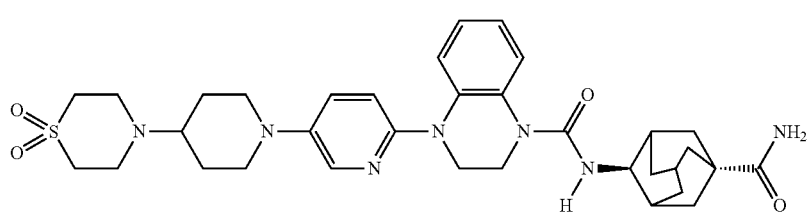 [SMILES: NC(=O)[C@]12CC3CC(C1)[C@H](NC(=O)N1CCN(c4ccc(N5CCC(N6CCS(=O)(=O)CC6)CC5)cn4)c4ccccc41)C(C3)C2]

3.1: tert-Butyl ester of 4-(1,1-dioxo-1lambda6-thiomorpholin-4-yl)-piperidine-1-carboxylic acid 1.473 g of boc-4-piperidone is put in 45 ml of methanol. 1 g of thiomorpholine-1,1-dioxide and 0.47 ml of acetic acid are added at room temperature. A weight increase is observed. Therefore methanol is added until stirring is correct. 0.511 g of sodium cyanoborohydride is then added. It is stirred at room temperature for 18 h and then the solution is heated under reflux for 3 h. The solution is then evaporated to dryness and the raw product obtained is chromatographed on silica gel, eluting with a gradient of ethyl acetate in heptane ranging from 20 to 100%. 0.786 g of tert-butyl ester of 4-(1,1-dioxo-1lambda6-thiomorpholin-4-yl)-piperidine-1-carboxylic acid is obtained.

$M-56+H^+=263$

3.2: 4-Piperidin-4-yl-thiomorpholine 1,1-dioxide 0.786 g of tert-butyl ester of 4-(1,1-dioxo-1lambda6-thiomorpholin-4-yl)-piperidine-1-carboxylic acid is put in 5 ml of dichloromethane. 12.3 ml of 4M hydrochloric acid in dioxane is added at room temperature. The solution is stirred for 18 h and evaporated to dryness. The product thus obtained is returned to the basic state by means of tetraalkylammonium carbonate resin at a rate of 2 g per mmol. 0.555 g of 4-piperidin-4-yl-thiomorpholine 1,1-dioxide is obtained.

3.3: tert-Butyl ester of 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid 0.993 g of tert-butyl ester of 4-(5-bromo-pyridin-2-yl)-3,4-dihydro-2H-quinoxaline-1-carboxylic acid (intermediate 1.1) is put in 12 mL of toluene. 0.555 g of 4-piperidin-4-yl-thiomorpholine 1,1-dioxide, 0.342 g of sodium tert-butylate, 0.167 g of 2-dicyclohexylphosphino-2',6'-dimethoxybiphenyl and 0.093 g of tris(dibenzylideneacetone)dipalladium (0) are added at room temperature and the reaction mixture is heated for 3 h at 110° C. Then ethyl acetate is added and the mixture is decanted. The aqueous phase is extracted a second time with ethyl acetate and the organic phases are washed with water. They are then dried over magnesium sulfate and concentrated under reduced pressure. The raw product obtained is chromatographed on silica gel, eluting with a gradient of methanol in dichloromethane ranging from 1% to 10%. 0.86 g of tert-butyl ester of 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid is obtained.

$M+H^+=528$

3.4: 1-[4-(1,1-Dioxo-1lambda6-thiomorpholin-4-yl)-3,4,5,6-tetrahydro-2H-[1,3']bipyridinyl-6'-yl]-1,2,3,4-tetrahydroquinoxaline hydrochloride 0.4 g of tert-butyl ester of 4-[4-(1,1-dioxo-1lambda6-thiomorpholin-4-yl)-3,4,5,6-tetrahydro-2H-[1,3']bipyridinyl-6'-yl]-3,4-dihydro=2H-quinoxaline-1-carboxylic acid is put in 4 ml of dichloromethane. 3.79 mL of 4M hydrochloric acid in dioxane is added at room temperature. The solution is stirred for 2 days. It is evaporated to dryness. 0.38 g of 1-[4-(1,1-dioxo-1lambda6-thiomorpholin-4-yl)-3,4,5,6-tetrahydro-2H-[1,3']bipyridinyl-6'-yl]-1,2,3,4-tetrahydroquinoxaline hydrochloride is obtained.

$M+H^+=428$ 3.5: trans-(5-Carbamoyl-adamantan-2-yl)-amide of 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid 0.379 g of 1-[4-(1,1-dioxo-1lambda6-thiomorpholin-4-yl)-3,4,5,6-tetrahydro-2H-[1,3']bipyridinyl-6'-yl]-1,2,3,4-tetrahydroquinoxaline hydrochloride in 13 mL of a saturated solution of sodium hydrogen carbonate is put in a 100-ml flask. 13 ml of dichloromethane is added. The solution is cooled in an ice bath. 0.6 ml of a solution of phosgene at 20% in toluene is added at +5° C. After 30 minutes, a fresh 0.6 ml of phosgene at 20% in toluene is added, then 30 minutes later, again 0.6 ml of phosgene at 20% in toluene is added. The reaction mixture is decanted 30 minutes later. Dichloromethane is added to the aqueous phase and it is decanted again. The organic phases are then combined, dried over magnesium sulfate, filtered and evaporated to dryness. This raw reaction product is taken up in 13 mL of dimethylformamide. 0.66 mL of diisopropylethylamine is added. 0.175 g of amide of trans-4-amino-adamantane-1-carboxylic acid is added. The solution is then stirred for 18 h and the reaction mixture is poured into water and extracted twice with ethyl acetate. The organic phase is washed twice with water, dried over magnesium sulfate, filtered and evaporated to dryness. The raw product obtained is chromatographed on silica gel, eluting with a gradient of methanol in dichloromethane ranging from 1% to 10%. 0.115 g of trans-(5-carbamoyl-adamantan-2-yl)-amide of 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid is obtained after trituration in ethyl ether with a few drops of ethyl acetate.
M+H$^{+=648}$, MP=160-200° C.;
$^1$H NMR (400 MHz, DMSO-d6) δ(ppm)=8.04 (m, 1H), 7.42 (m, 2H), 7.10 (m, 2H), 6.95 (m, 2H), 6.86 (m, 1H), 6.68 (s.broad, 1H), 6.05 (d, J=6 Hz, 1H), 3.87 to 3.63 (m, 7H), 3.04 (m, 8H), 2.68 (m, 3H), 2.12 to 1.34 (m, 17H).

Example 4

Trans 4-[5-(1,1-difluoro-6-aza-spiro[2.5]oct-6-yl)-pyridin-2-yl]-3,4-dihydro-2H-quinoxaline-1-carboxylic acid (5-carbamoyl-adamantan-2-yl)-amide; (trans (5-Carbamoyl-adamantan-2-yl)-amide hydrochloride of 4-[5-(1,1-difluoro-6-aza-spiro[2.5]oct-6-yl)-pyridin-2-yl]-3,4-dihydro-2H-quinoxaline-1-carboxylic acid) (compound No. 11)

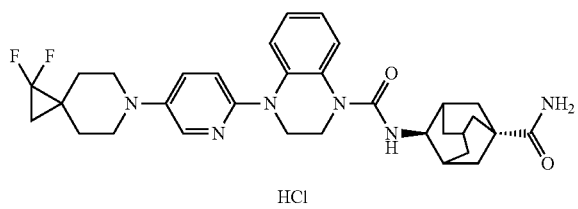 [SMILES: NC(=O)[C@]12CC3CC(C1)[C@H](NC(=O)N1CCN(c4ccc(N5CCC6(CC5)CC6(F)F)cn4)c4ccccc41)C(C3)C2 ; Cl]

HCl 4.1: tert-Butyl ester of 1,1-difluoro-6-aza-spiro[2.5]octane-6-carboxylic acid 5.07 g of trimethylsilyl-2,2-difluoro-2-(fluorosulfonyl)acetate and 0.025 g of sodium fluoride are put in a 50-ml flask. The reaction mixture is cooled with an ice bath and 2 g of 1-N-boc-4-methylenepiperidine is added dropwise. The reaction mixture is then heated to 105° C. Once this temperature is reached, strong evolution of gas is observed and the solution turns very dark orange. The heating is then stopped and, once cooled, the reaction mixture is poured into a solution of sodium hydrogen carbonate. It is extracted twice with dichloromethane and the organic phase is washed twice with water. It is dried over magnesium sulfate, filtered and concentrated to dryness. The raw product obtained is chromatographed on silica gel, eluting with a gradient of ethyl acetate in heptane ranging from 0 to 30%. 1.2 g of tert-butyl ester of 1,1-difluoro-6-aza-spiro[2.5]octane-6-carboxylic acid is obtained.
M−56+ACN+H$^{+=233}$ 4.2: 1,1-Difluoro-6-aza-spiro[2.5]octane hydrochloride 1.2 g of tert-butyl ester of 1,1-difluoro-6-aza-spiro[2.5]octane-6-carboxylic acid is put in 24 mL of dichloromethane. 24 mL of 4M hydrochloric acid in dioxane is added at room temperature. The solution is stirred for 4 h and is evaporated to dryness. 1 g of 1,1-difluoro-6-aza-spiro[2.5]octane hydrochloride is obtained.

4.3: tert-Butyl ester of 4-[5-(1,1-difluoro-6-aza-spiro[2.5]oct-6-yl)-pyridin-2-yl]-3,4-dihydro-2H-quinoxaline-1-carboxylic acid 0.894 g of 1,1-difluoro-6-aza-spiro[2.5]octane hydrochloride is put in 22 ml of toluene. 1.12 g of sodium tert-butylate, 1.9 g of tert-butyl ester of 4-(5-bromo-pyridin-2-yl)-3,4-dihydro-2H-quinoxaline-1-carboxylic acid (intermediate 1.1), 0.32 g of 2-dicyclohexylphosphino-2',6'-dimethoxybiphenyl and 0.178 g of tris(dibenzylideneacetone)dipalladium (0) are added at room temperature. It is heated for 3 h at 105° C. Then ethyl acetate is added and the mixture is decanted. It is extracted twice more with ethyl acetate and the organic phases are washed with water twice. They are then dried over magnesium sulfate and concentrated under reduced pressure. The raw product obtained is chromatographed on silica gel, eluting with a gradient of ethyl acetate in heptane ranging from 10% to 70%. 1.48 g of tert-butyl ester of 4-[5-(1,1-difluoro-6-aza-spiro[2.5]oct-6-yl)-pyridin-2-yl]-3,4-dihydro-2H-quinoxaline-1-carboxylic acid is obtained.
M+H$^{+=457}$ 4.4 1-[5-(1.1-Difluoro-6-aza-spiro[2.5]oct-6-yl)-pyridin-2-yl]-1,2,3,4-tetrahydroquinoxaline 1.48 g of tert-butyl ester of 4-[5-(1,1-difluoro-6-aza-spiro[2.5]oct-6-yl)-pyridin-2-yl]-3,4-dihydro-2H-quinoxaline-1-carboxylic acid is put in 16 mL of dichloromethane. 24 mL of 4M hydrochloric acid in dioxane is added at +4° C. The solution is stirred at room temperature for 4 h and evaporated to dryness. The residue is taken up in a saturated solution of sodium hydrogen carbonate to basic pH. The solution is extracted twice with dichloromethane, washed with water, dried over magnesium sulfate, filtered and evaporated to dryness. 1.4 g of 1-[5-(1,1-difluoro-6-aza-spiro[2.5]oct-6-yl)-pyridin-2-yl]-1,2,3,4-tetrahydroquinoxaline is obtained.
M+H$^{+=357}$ 4.5 trans-(5-Carbamoyl-adamantan-2-yl)-amide hydrochloride of 4-[5-(1,1-difluoro-6-aza-spiro[2.5]oct-6-yl)-pyridin-2-yl]-3,4-dihydro-2H-quinoxaline-1-carboxylic acid 1.17 g of 1-[5-(1,1-difluoro-6-aza-spiro[2.5]oct-6-yl)-pyridin-2-yl]-1,2,3,4-tetrahydroquinoxaline is added to 9 mL of dichloromethane in a 50-ml three-necked flask under inert atmosphere of nitrogen. 1.1 ml of triethylamine is added at 0° C. Then 0.304 g of triphosgene is added. The reaction mixture is stirred for 30 minutes at 0° C. and then at room temperature for 3 h. 0.89 mL of triethylamine is added again and 0.65 g of amide of trans-4-amino-adamantane-1-carboxylic acid is then added. For better solubility, 23 mL of dimethylformamide is added. The solution is stirred at room temperature for 18 h and is then poured into water and extracted twice with dichloromethane. The organic phases are combined and washed twice with water, dried over magnesium sulfate, filtered and evaporated to dryness. The raw product obtained is chromatographed on silica gel, eluting with a gradient of methanol in dichloromethane ranging from 1% to 10%. Therefore 0.428 g of trans-(5-carbamoyl-adamantan-2-yl)-amide of 4-[5-(1,1-difluoro-6-aza-spiro[2.5]oct-6-yl)-pyridin-2-yl]-3,4-dihydro-2H-quinoxaline-1-carboxylic acid is obtained, which is then dissolved in 4 mL of dichloromethane, to which 3.5 mL of a solution 0.2N of hydrochloric acid in ethyl ether is added, with stirring. It is evaporated to dryness and is taken up in ethyl acetate. A precipitate is obtained, which is drained and then dried under vacuum at 40° C. 0.37 g of trans-(5-carbamoyl-adamantan-2-yl)-amide hydrochloride of 4-[5-(1,1-difluoro-6-aza-spiro[2.5]oct-6-yl)-pyridin-2-yl]-3,4-dihydro-2H-quinoxaline-1-carboxylic acid is obtained.

M+H$^{+}$=577; MP=134-170° C.;

$^1$H NMR (400 MHz, DMSO-d6) δ(ppm)=8.09 (broad singlet, 1H), 7.77 (m, 1H), 7.53 (m, 1H), 7.26 (m, 1H), 7.19 (m, 1H), 6.99 (m, 3H), 6.69 (broad singlet, 1H), 6.16 (d, J=5.8 Hz, 1H), 3.86 (m, 4H), 3.74 (m, 1H), 3.30 (m, 4H), 2.00 (m, 3H), 1.94 to 1.64 (m, 12H), 1.45 (m, 2H), 1.38 (m, 2H).

Example 5 trans-6-{6-[4-(5-Carbamoyl-adamantan-2-ylcarbamoyl)-3,4-dihydro-2H-quinoxalin-1-yl]-pyridin-3-yl}-6-aza-spiro[2.5]octane-1-carboxylic acid (compound No. 12)

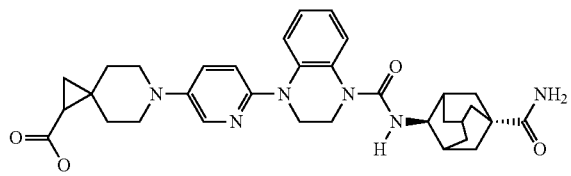 [SMILES: NC(=O)[C@]12CC3CC(C1)[C@H](NC(=O)N1CCN(c4ccc(N5CCC6(CC5)CC6C(=O)O)cn4)c4ccccc41)C(C3)C2]

5.1: 6'-(3,4-Dihydro-2H-quinoxalin-1-yl)-2,3,5,6-tetrahydro-[1,3']-bipyridinyl-4-one In a 150-ml flask, 5.51 g of tert-butyl ester of 4-[5-(1,4-dioxa-8-aza-spiro[4.5]dec-8-yl)-pyridin-2-yl]-3,4-dihydro-2H-quinoxaline-1-carboxylic acid (intermediate 7.1) is put in 21 ml of tetrahydrofuran, 21 ml of water and 20 ml of acetone. It is cooled on an ice bath and 8.24 ml of 95% sulfuric acid is added gently. It is stirred at room temperature for 18 h. The solution is then poured into water. 5N sodium hydroxide is added to basic pH and it is extracted twice with ethyl acetate. The combined organic phases are washed with water, dried over sodium sulfate, filtered and evaporated to dryness. The raw product obtained is chromatographed on silica gel, eluting with a gradient of ternary solvents, on the one hand heptane and on the other hand heptane/ethyl acetate/methanol 4/5/1 varying from 10% to 100%. 2.39 g of 6'-(3,4-dihydro-2H-quinoxalin-1-yl)-2,3,5,6-tetrahydro-[1,3']bipyridinyl-4-one is obtained.

M+H$^{+}$=309

5.2: Ethyl ester of [6'-(3,4-dihydro-2H-quinoxalin-1-yl)-2,3,5,6-tetrahydro-[1,3']bipyridinyl-4-ylidene]-acetic acid 1.91 g of triethylphosphonoacetate and 19 mL of anhydrous tetrahydrofuran are put in a 100-ml flask. It is cooled on an ice bath. At +5° C., 0.205 g of 95% sodium hydride is added a little at a time with a spatula. After addition, it is returned to room temperature and the reaction mixture is stirred for 30 minutes. Then the flask is immersed in an ice bath and 0.205 g of 95% sodium hydride is added at +5° C. It is stirred for 30 minutes at room temperature. 2.39 g of 6'-(3,4-dihydro-2H-quinoxalin-1-yl)-2,3,5,6-tetrahydro-[1,3']bipyridinyl-4-one and 19 mL of anhydrous tetrahydrofuran are put in another 100-ml flask. Again at +5° C., the solution of ylide is added to the solution of 6'-(3,4-dihydro-2H-quinoxalin-1-yl)-2,3,5,6-tetrahydro-[1,3']bipyridinyl-4-one. It is allowed to return to room temperature and it is stirred for 18 h. The reaction mixture is poured into water and it is extracted three times with ethyl acetate. The organic phases are washed with water, dried over magnesium sulfate, filtered and evaporated to dryness. The raw product obtained is first chromatographed on silica gel, eluting with a gradient of ternary solvents, on the one hand heptane and on the other hand heptane/ethyl acetate/methanol 4/5/1 varying from 10% to 100%. The product obtained is chromatographed again on silica gel with a gradient of methanol in dichloromethane ranging from 1% to 10%. 0.468 g of ethyl ester of [6'-(3,4-dihydro-2H-quinoxalin-1-yl)-2,3,5,6-tetrahydro-[1,3']bipyridinyl-4-ylidene]-acetic acid is obtained. As for the aqueous phase, it contains [6'-(3,4-dihydro-2H-quinoxalin-1-yl)-2,3,5,6-tetrahydro-[1,3']bipyridinyl-4-ylidene]-acetic acid, which is recovered by adding a saturated solution of sulfurous acid in water and extracting with dichloromethane and ethyl acetate. The organic phase thus obtained is dried over sodium sulfate, filtered and evaporated to dryness. 1.08 g of [6'-(3,4-dihydro-2H-quinoxalin-1-yl)-2,3,5,6-tetrahydro-[1,3']bipyridinyl-4-ylidene]-acetic acid is obtained. This 1.08 g of acid is then reesterified with 0.90 ml of sulfuric acid in 15 ml of ethanol under reflux for 3 h. The reaction mixture is then poured into water+ice. Sodium hydrogen carbonate is added to pH 8. It is extracted twice with ethyl acetate, and washed with water and with water saturated with sodium chloride. It is dried over magnesium sulfate, filtered and evaporated to dryness. The raw product obtained is chromatographed on silica gel, eluting with a gradient of methanol in dichloromethane ranging from 1% to 10%. 0.736 g of ethyl ester of [6'-(3,4-dihydro-2H-quinoxalin-1-yl)-2,3,5,6-tetrahydro-[1,3']bipyridinyl-4-ylidene]-acetic acid is obtained. The total amount obtained is therefore 1.2 g of ethyl ester of [6'-(3,4-dihydro-2H-quinoxalin-1-yl)-2,3,5,6-tetrahydro-[1,3']bipyridinyl-4-ylidene]-acetic acid.

M+H$^{+}$=379

5.3: Ethyl ester of 6-[6-(3,4-dihydro-2H-quinoxalin-1-yl)-pyridin-3-yl]-6-aza-spiro[2.5]octane-1-carboxylic acid 1.04 g of trimethylsulfoxonium iodide in 15 mL of dimethylsulfoxide is put in a 150-ml flask. 0.533 g of potassium tertbutylate is added at room temperature. It is stirred at room temperature for 3 h. A solution of 1.2 g of ethyl ester of

[6'-(3,4-dihydro-2H-quinoxalin-1-yl)-2,3,5,6-tetrahydro-[1,3']bipyridinyl-4-ylidene]-acetic acid dissolved in 15 ml of dimethylsulfoxide is added. It is stirred at room temperature for 3 h and is left to stand for 2 days. Trimethylsulfoxonium iodide (0.78 g) in 8 mL of dimethylsulfoxide is prepared again, and 0.4 g of potassium tertbutylate is added to the solution. It is stirred for 3 h. Then this solution is added to the reaction mixture and it is stirred at room temperature for 18 h. The solution is then poured into water and extracted three times with ethyl acetate. The combined organic phases are dried over sodium sulfate, filtered and evaporated to dryness. The raw product obtained is chromatographed on silica gel, eluting with a gradient of methanol in dichloromethane ranging from 0.5% to 5%. The product is chromatographed on silica gel again, eluting with a gradient of ternary solvents, on the one hand dichloromethane and on the other hand dichloromethane/ethyl acetate/methanol 70/25/5 varying from 10% to 100%. 0.338 g of ethyl ester of 6-[6-(3,4-dihydro-2H-quinoxalin-1-yl)-pyridin-3-yl]-6-aza-spiro[2.5]octane-1-carboxylic acid is obtained.
$M+H^{+=393}$ 5.4: Ethyl ester of trans-6-{6-[4-(5-carbamoyl-adamantan-2-ylcarbamoyl)-3,4-dihydro-2H-quinoxalin-1-yl]-pyridin-3-yl}-6-aza-spiro[2.5]octane-1-carboxylic acid 0.338 g of ethyl ester of 6-[6-(3,4-dihydro-2H-quinoxalin-1-yl)-pyridin-3-yl]-6-aza-spiro[2.5]octane-1-carboxylic acid in 8 mL of dichloromethane is put in a 50-ml three-necked flask under inert atmosphere of nitrogen. 0.36 mL of triethylamine is added at 0° C. Then 0.102 g of triphosgene is added at 0° C. The reaction mixture is stirred for 30 minutes at 0° C. and then at room temperature for 3 h. 0.30 mL of triethylamine is added again and 0.22 g of amide of trans-4-aminoadamantane-1-carboxylic acid is then added. For better solubility, 8 mL of dimethylformamide is added. The solution is stirred at room temperature for 18 h. It is then poured into water and extracted twice with dichloromethane. The organic phases are combined and washed three times with water, dried over magnesium sulfate, filtered and evaporated to dryness. The raw product obtained is chromatographed on silica gel, eluting with a gradient of ternary solvents, on the one hand heptane and on the other hand heptane/ethyl acetate/methanol 4/5/1 varying from 10% to 100%. 0.343 g of ethyl ester of trans-6-{6-[4-(5-carbamoyl-adamantan-2-ylcarbamoyl)-3,4-dihydro-2H-quinoxalin-1-yl]-pyridin-3-yl}-6-aza-spiro[2.5]octane-1-carboxylic acid is obtained.
$M+H^{+=613}$ 5.5: trans-6-{6-[4-(5-Carbamoyl-adamantan-2-ylcarbamoyl)-3,4-dihydro-2H-quinoxalin-1-yl]-pyridin-3-yl}-6-aza-spiro[2.5]octane-1-carboxylic acid 0.343 g of ethyl ester of trans-6-{6-[4-(5-carbamoyl-adamantan-2-ylcarbamoyl)-3,4-dihydro-2H-quinoxalin-1-yl]-pyridin-3-yl}-6-aza-spiro[2.5]octane-1-carboxylic acid in 6 ml of a 1/1/1 mixture of tetrahydrofuran/methanol/water is put in a 50-ml flask. 0.090 g of lithium hydroxide monohydrate is added at room temperature. It is stirred at room temperature for 18 h. It is evaporated to dryness. It is taken up in water and a saturated solution of sulfurous acid in water is added until the pH is acid. A precipitate forms. It is drained and dried under vacuum at 40° C. 0.214 g of trans-6-{6-[4-(5-carbamoyl-adamantan-2-ylcarbamoyl)-3,4-dihydro-2H-quinoxalin-1-yl)-pyridin-3-yl}-6-aza-spiro[2.5]octane-1-carboxylic acid is obtained.

$M+H^{+=585}$; MP=145-160° C.;
$^1$H NMR (400 MHz, DMSO-d6) δ(ppm)=12.09 (m, 1H), 8.04 (d, J=3 Hz, 1H), 7.41 (m, 2H), 7.09 (m, 2H), 7.00 to 6.80 (m, 3H), 6.68 (m, 1H), 6.05 (d, J=6 Hz, 1H), 3.94 to 3.68 (m, 5H), 3.42 to 2.92 (m, 4H), 2.05 to 1.37 (m, 18H), 0.96 (m, 2H).

Example 6

Trans 4-[5-(4-methyl-4-phenyl-[1,4]azasilinan-1-yl)-pyridin-2-yl]-3,4-dihydro-2H-quinoxaline-1-carboxylic acid (5-carbamoyl-adamantan-2-yl)-amide; (trans-(5-Carbamoyl-adamantan-2-yl)-amide of 4-[5-(4-methyl-4-phenyl-[1,4]azasilinan-1-yl)-pyridin-2-yl]-3,4-dihydro-2H-quinoxaline-1-carboxylic acid) (compound No. 13)

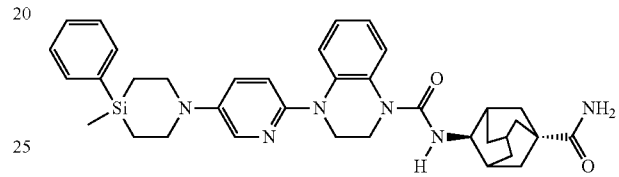

6.1: Methyl-phenyl-divinyl-silane 158 ml of a solution of vinylmagnesium chloride in THF is added dropwise using a dropping funnel in 1 h at room temperature under nitrogen to 13.1 ml of a solution of dimethoxymethylphenyldivinylsilane in 36 ml of anhydrous THF. The temperature is controlled with a water bath. After addition, the mixture is stirred at room temperature for 16 h and then refluxed for 2 h. 40 ml of $H_2O$ is then added and the mixture is stirred for 30 min. The white precipitate that forms is filtered and is then rinsed with ethyl acetate. The filtrate is extracted with ethyl acetate twice. The organic phases are combined, washed with a saturated aqueous solution of sodium chloride, dried over magnesium sulfate and concentrated under vacuum. 12.56 g of methyl-phenyl-divinyl-silane is obtained in the form of a clear yellow oil, which is then used without further purification.
$^1$H NMR (CDCl$_3$, 200 MHz), δ(ppm)=0.45 (s, 3H); 5.80 (dd, J=19.6 and 4.5 Hz, 2H); 6.14 (dd, J=14.6 and 4.5 Hz, 2H); 6.34 (dd, J=19.6 and 14.6 Hz, 2H); 7.40-7.27 (m, 3H); 7.58-7.53 (m, 2H).

6.2: 2-[(2-Hydroxy-ethyl)-methyl-phenyl-silanyl]-ethyl alcohol 16.1 g of methyl-phenyl-divinyl-silane is put in 65 ml of anhydrous THF under nitrogen at room temperature. 24.6 g of 9-BBN dimer is added and the mixture is refluxed for 4 h. On return to room temperature, 40 ml of $H_2O$ is added, followed by 90 ml of a 3N soda solution. The mixture is cooled to 0° C. and 90 ml of a 30% solution of hydrogen peroxide is added cautiously. The mixture is then refluxed for 2 h. The two-phase mixture is extracted with ethyl acetate three times. The organic phases are combined, washed with a saturated aqueous solution of sodium chloride, dried over magnesium sulfate and concentrated under vacuum. The raw product obtained is chromatographed on silica gel, eluting with a gradient of ethanol and of dichloromethane in heptane ranging from 0.4/3.6/6 to 0.4/4.4/5. 15.1 g of 2-[(2-hydroxy-ethyl)-methyl-phenyl-silanyl]-ethyl alcohol is obtained in the form of a white solid.

$^1$H NMR (CDCl$_3$, 200 MHz), δ(ppm)=0.36 (s, 3H); 1.27 (t, J=7.5 Hz, 4H); 2.11 (s broad, 2H); 3.80 (t, J=7.5 Hz, 4H); 7.40-7.36 (m, 3H); 7.55-7.50 (m, 2H).

6.3: 1-Benzyl-4-methyl-4-phenyl-[1,4]azasilinane 8.5 g of 2-[(2-hydroxy-ethyl)-methyl-phenyl-silanyl]-ethyl alcohol is put in 80 ml of anhydrous dichloromethane under nitrogen. 14.2 ml of triethylamine is added, and then, at 0° C., 6.9 ml of mesyl chloride is added dropwise using a dropping funnel. The mixture is stirred for 2 h at 0° C. and gradually turns orange with appearance of a precipitate. Once conversion is complete, 14.2 ml of triethylamine is added and then 4.7 ml of benzylamine at 0° C. The reaction mixture is brought back to room temperature and then refluxed for 6 h. After hydrolysis with H$_2$O at room temperature, the reaction mixture is extracted with ethyl acetate three times. The organic phases are combined, washed with a saturated aqueous solution of sodium chloride, dried over magnesium sulfate and concentrated under vacuum. The raw product obtained is chromatographed on silica gel, eluting with a gradient of ethyl acetate and heptane containing 3% of triethylamine varying from 0/10 to 3/7. 3.6 g of 1-benzyl-4-methyl-4-phenyl-[1,4]azasilinane is obtained in the form of a clear yellow oil.

$^1$H NMR (CDCl$_3$, 200 MHz), δ(ppm): 0.32 (s, 3H); 1.00-0.86 (m, 2H); 1.35-1.15 (m, 2H); 2.82 (s broad, 4H); 3.62 (s broad, 2H); 7.40-7.27 (m, 8H); 7.59-7.54 (m, 2H).

6.4: 4-Methyl-4-phenyl-[1,4]azasilinane hydrochloride 3.6 g of 1-benzyl-4-methyl-4-phenyl-[1,4]azasilinane is put in 32 ml of anhydrous dichloromethane under nitrogen. At 0° C., 2.5 ml of 1-chloroethyl chloroformate is added dropwise to the reaction mixture. The reaction mixture is gradually brought back to room temperature and then stirred for 2 h under reflux. After complete conversion, the reaction mixture is concentrated under vacuum and dried, then the residue is dissolved in 50 ml of methanol at room temperature. The mixture is stirred under reflux for 2 h. After evaporation of the solvent under vacuum, the yellow solid obtained is then suspended in ethyl acetate. The suspension is refluxed for some minutes and then gradually cooled to room temperature. The crystals thus formed are filtered, washed with ethyl acetate and dried under vacuum. 2.13 g of 4-methyl-4-phenyl-[1,4] azasilinane hydrochloride is obtained in the form of white crystals.

MP=245° C.; M+H$^{+=191}$;
$^1$H NMR (DMSO, 200 MHz), δ(ppm)=0.40 (s, 3H); 1.11 (dt, J=15.1 and 5.4 Hz, 2H); 1.33 (dd, J=15.1 and 6.7 Hz, 2H); 3.31-3.23 (m, 4H); 7.46-7.38 (m, 3H); 7.62-7.57 (m, 2H); 8.79 (s broad, 2H).

6.5: tert-Butyl ester of 4-[5-(4-methyl-4-phenyl-[1,4]azasilinan-1-yl)-pyridin-2-yl]-3,4-dihydro-2H-quinoxaline-1-carboxylic acid 0.5 g of tert-butyl ester of 4-(5-bromo-pyridin-2-yl)-3,4-dihydro-2H-quinoxaline-1-carboxylic acid (intermediate 1.1) is put in 6.5 ml of toluene and then 0.21 g of 2-dicyclohexylphosphino-2',6'-dimethoxybiphenyl, 0.117 g of tris(dibenzylideneacetone)dipalladium (0), 0.307 g of sodium tert-butylate and 0.321 g of 4-methyl-4-phenyl[1,4]azasilinane hydrochloride are added. The reaction mixture is heated at 105-110° C. for 19 h. After concentration, ethyl acetate is added and the mixture is washed with an aqueous solution of sodium chloride and then with water. The organic phase is dried over sodium sulfate and concentrated under reduced pressure. The raw product obtained is chromatographed on silica gel, eluting with a gradient of heptane/ethyl acetate solvents (100/0 to 70/30). 0.43 g of tert-butyl ester of 4-[5-(4-methyl-4-phenyl-[1,4]azasilinan-1-yl)-pyridin-2-yl]-3,4-dihydro-2H-quinoxaline-1-carboxylic acid is obtained.

M+H$^{+=501.1}$

6.6: 1-[5-(4-Methyl-4-phenyl-[1,4]azasilinan-1-yl)-pyridin-2-yl]-1,2,3,4-tetrahydroquinoxaline 0.43 g of tert-butyl ester of 4-[5-(4-methyl-4-phenyl-[1,4] azasilinan-1-yl)-pyridin-2-yl]-3,4-dihydro-2H-quinoxaline-1-carboxylic acid is put in 50 mL of dichloromethane and after cooling on an ice bath, 3.5 mL of a 4N solution of hydrochloric acid in dioxane is added. The reaction mixture is stirred for 16 h. After concentration, the mixture is taken up in dichloromethane, and neutralized by adding a saturated solution of sodium bicarbonate. After decanting, the aqueous phase is extracted with dichloromethane. The dichloromethane phases are combined and dried over sodium sulfate. After concentration under vacuum, 0.338 g of 1-[5-(4-methyl-4-phenyl[1,4]azasilinan-1-yl)-pyridin-2-yl]-1,2,3,4-tetrahydroquinoxaline is obtained.

M+H$^{+=401.1}$

6.7: trans-(5-Carbamoyl-adamantan-2-yl)-amide of 4-[5-(4-methyl-4-phenyl-[1,4]azasilinan-1-yl)-pyridin-2-yl)-3,4-dihydro-2H-quinoxaline-1-carboxylic acid 0.338 g of 1-[5-(4-methyl-4-phenyl-[1,4]azasilinan-1-yl)-pyridin-2-yl]-1,2,3,4-tetrahydroquinoxaline and 15 ml of dichloromethane are put in a three-necked flask under nitrogen atmosphere. 0.35 mL of triethylamine is added. The mixture is cooled with an ice/acetone mixture to −8° C. and then 0.133 g of triphosgene is added. The reaction mixture is then stirred at room temperature for 3 h. 10 ml of dimethylformamide, 0.193 g of amide hydrochloride of trans-4-amino-adamantane-1-carboxylic acid and 0.35 ml of triethylamine are put in a flask. The mixture is placed in an ultrasonic cell and then heated to obtain an almost clear mixture. This mixture is added a little at a time to previously prepared carbamoyl chloride, which is cooled with a water bath. The reaction mixture is stirred at room temperature for 16 h. After evaporation of the dichloromethane, the reaction mixture is taken up in 300 ml of ethyl acetate and washed with a saturated solution of sodium chloride. The organic phase is dried over sodium sulfate and then concentrated under vacuum. The raw product obtained is chromatographed on silica gel, eluting with a gradient of dichloromethane/methanol solvents (100/0 to 90/10). 0.28 g of trans-(5-carbamoyl-adamantan-2-yl)-amide of 4-[5-(4-methyl-4-phenyl-[1,4]azasilinan-1-yl)-pyridin-2-yl]-3,4-dihydro-2H-quinoxaline-1-carboxylic acid is obtained.

M+H$^{+=621}$; MP=106-108° C.;
$^1$H NMR (400 MHz, DMSO-d6) δ(ppm)=8.05 (d, J=3.1 Hz, 1H), 7.52 (m, 2H), 7.43 to 7.31 (m, 5H), 7.11 (d, J=9 Hz, 1H), 7.03 (dd, J=8.1 Hz and 1.5 Hz, 1H), 6.98 (m, 1H), 6.92 (m, 1H), 6.81 (m, 1H), 6.69 (m, 1H), 6.03 (d, J=6.2 Hz, 1H), 3.83 to 3.61 (m, 9H), 2.02 to 1.69 (m, 11H), 1.46 (m, 2H), 1.12 (m, 2H), 0.94 (m, 2H), 0.35 (s, 3H).

Example 7

Trans 4-[4-((R)-3-hydroxy-pyrrolidin-1-yl)-3,4,5,6,-tetrahydro-2H-[1,3']bipyridinyl-6'-yl]-3,4-dihydro-2H-quinoxaline-1-carboxylic acid (5-carbamoyl-adamantan-2-yl)-amide; trans-(5-Carbamoyl-adamantan-2-yl)-amide hydrochloride of 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid (compound No. 9)

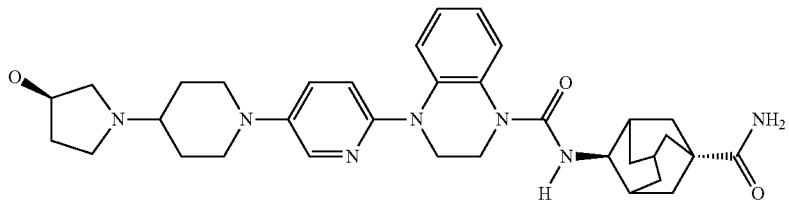 [SMILES: NC(=O)[C@]12CC3CC(C1)[C@H](NC(=O)N1CCN(c4ccc(N5CCC(N6CC[C@@H](O)C6)CC5)cn4)c4ccccc41)C(C3)C2]

7.1: tert-Butyl ester of 4-[5-(1,4-dioxa-8-aza-spiro[4.5]dec-8-yl)-pyridin-2-yl]-3,4-dihydro-2H-quinoxaline-1-carboxylic acid 2 g of tert-butyl ester of 4-(5-bromo-pyridin-2-yl)-3,4-dihydro-2H-quinoxaline-1-carboxylic acid (intermediate 1.1) is put in 25 ml of toluene. 0.81 g of 1,4-dioxa-8-aza-spiro[4.5]decane, 0.69 g of sodium tert-butoxide, 0.34 g of 2-dicyclohexylphosphino-2',6'-dimethoxybiphenyl and 0.19 g of tris(dibenzylideneacetone)dipalladium (0) are added. The reaction mixture is stirred for 2 h under nitrogen at 110° C. The reaction mixture is poured into 200 ml of $H_2O$, and extracted twice with 150 ml of ethyl acetate. The organic phases are combined, washed twice with 100 ml of $H_2O$, then with 100 ml of a saturated aqueous solution of sodium chloride, dried over $MgSO_4$ and concentrated to dryness. The raw product obtained is chromatographed on silica gel, eluting with a gradient of ethyl acetate in heptane, varying from 5% to 50%. 2.4 g of tert-butyl ester of 4-[5-(1,4-dioxa-8-aza-spiro[4.5]dec-8-yl)-pyridin-2-yl]-3,4-dihydro-2H-quinoxaline-1-carboxylic acid is obtained.

$[M+H^+]=453$

7.2: 1-[5-(1,4-Dioxa-8-aza-spiro[4.5]dec-8-yl)-pyridin-2-yl]-1,2,3,4-tetrahydroquinoxaline 2.7 g of tert-butyl ester of 4-[5-(1,4-dioxa-8-aza-spiro[4.5]dec-8-yl)-pyridin-2-yl]-3,4-dihydro-2H-quinoxaline-1-carboxylic acid is put in 30 ml of dioxane, then 22.37 ml of 4N HCl in dioxane is added. The reaction mixture is stirred for 48 h in a closed environment at room temperature. After concentration to dryness, the reaction mixture is diluted with 200 ml of a saturated aqueous solution of sodium hydrogen carbonate and extracted twice with 200 ml of dichloromethane. The resultant organic phases are combined, washed with 100 ml of a saturated aqueous solution of sodium hydrogen carbonate, and with 100 ml of a saturated aqueous solution of sodium chloride, dried over $MgSO_4$ and concentrated to dryness. 2.1 g of 1-[5-(1,4-dioxa-8-aza-spiro[4.5]dec-8-yl)-pyridin-2-yl]-1,2,3,4-tetrahydroquinoxaline is obtained.

$[M+H^+]=353$

7.3: trans-(5-Carbamoyl-adamantan-2-yl)-amide of 4-[5-(1,4-dioxa-8-aza-spiro[4.5]dec-8-yl)-pyridin-2-yl]-3,4-dihydro-2H-quinoxaline-1-carboxylic acid 2.25 g of 1-[5-(1,4-dioxa-8-aza-spiro[4.5]dec-8-yl)-pyridin-2-yl]-1,2,3,4-tetrahydroquinoxaline is put in 30 mL of dichloromethane at 0° C. 1.78 mL of triethylamine is added, and then 0.76 g of triphosgene. The reaction mixture is stirred for 30 min under nitrogen at 0° C., then for 3 hours at room temperature. Then 1.47 g of amide hydrochloride of trans-4-amino-adamantane-1-carboxylic acid, 2.22 ml of triethylamine and 30 ml of DMF are added. The reaction mixture is stirred for 18 h at room temperature under nitrogen. After hydrolysis with 250 ml of $H_2O$, the mixture is extracted twice with 350 mL of dichloromethane. The resultant organic phases are combined, washed twice with 200 ml of $H_2O$, then with 200 ml of a saturated aqueous solution of sodium chloride, dried over $MgSO_4$ and concentrated to dryness. The raw product obtained is chromatographed twice on silica gel, eluting with a gradient of methanol in dichloromethane ranging from 1% to 10%. 2.3 g of trans-(5-carbamoyl-adamantan-2-yl)-amide of 4-[5-(1,4-dioxa-8-aza-spiro[4.5]dec-8-yl)-pyridin-2-yl]-3,4-dihydro-2H-quinoxaline-1-carboxylic acid is obtained.

$[M+H^+]=573$; MP=177° C.

7.4: trans-(5-Carbamoyl-adamantan-2-yl)-amide of 4-(4-oxo-3,4,5,6-tetrahydro-2H-[1,3']bipyridinyl-6'-yl)-3,4-dihydro-2H-quinoxaline-1-carboxylic acid 2.1 g of trans-(5-carbamoyl-adamantan-2-yl)-amide of 4-[5-(1,4-dioxa-8-aza-spiro[4.5]dec-8-yl)-pyridin-2-yl]-3,4-dihydro-2H-quinoxaline-1-carboxylic acid is put in 40 ml of a 1/1 acetone/water mixture. 11.17 ml of concentrated sulfuric acid is slowly added. The reaction mixture is stirred for 48 h under nitrogen at room temperature. The reaction mixture is concentrated (evaporation of acetone), basified at 0° C. with an aqueous solution of 1M sodium hydroxide to pH 10 and then extracted 3 times with 200 ml of dichloromethane. The resultant organic phases are combined, washed with 200 mL of $H_2O$, then with 200 mL of a saturated aqueous solution of sodium chloride, dried over $MgSO_4$ and concentrated to dryness. 1.6 g of trans-(5-carbamoyl-adamantan-2-yl)-amide of 4-(4-oxo-3,4,5,6-tetrahydro-2H-[1,3']bipyridinyl-6'-yl)-3,4-dihydro-2H-quinoxaline-1-carboxylic acid is obtained.

$[M+H^+]=529$

7.5: trans-(5-Carbamoyl-adamantan-2-yl)-amide of 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid 0.2 g of trans-(5-carbamoyl-adamantan-2-yl)-amide of 4-(4-oxo-3,4,5,6-tetrahydro-2H-[1,3']bipyridinyl-6'-yl)-3,4-dihydro-2H-quinoxaline-1-carboxylic acid is put in 2 ml of dichloromethane. 0.034 g of (R)-pyrrolidin-3-ol alcohol is added, and then 0.096 g of sodium triacetoxyborohydride. The reaction mixture is stirred for 18 h under nitrogen at room temperature. The reaction mixture is diluted with 75 ml of dichloromethane, and washed with 75 ml of a saturated aqueous solution of sodium hydrogen carbonate. The aqueous phase is extracted with 75 ml of dichloromethane and the resultant organic phases are combined, washed with 50 mL of a saturated aqueous solution of sodium hydrogen carbonate, 50 ml of a saturated aqueous solution of sodium chloride, dried over $MgSO_4$ and concentrated to dryness. The raw product obtained is chromatographed on silica gel, eluting with a mixture of 10% of methanol in dichloromethane and then with a mixture of 2% of ammonia and 20% of methanol in dichloromethane. 0.19 g of trans-(5-carbamoyl-adamantan-2-yl)-amide of 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid is obtained.

$[M+H^+]=600$

7.6: trans-(5-Carbamoyl-adamantan-2-yl)-amide hydrochloride of 4-[4-((R)-3-hydroxy-pyrrolidin-1-yl)-3,4,5,6-tetrahydro-2H-[1,3']bipyridinyl-6'-yl]-3, 4-dihydro-2H-quinoxaline-1-carboxylic acid The trans-(5-carbamoyl-adamantan-2-yl)-amide of 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid (0.19 g, 0.32 mmol) is put in 5 mL of dichloromethane. 1.6 mL of a 0.2 M solution of hydrochloric acid in diethyl ether is added. The reaction mixture is concentrated to dryness, taken up in 5 mL of ethyl acetate, triturated and then filtered and dried under vacuum at 40° C. for 18 h. 0.18 g of trans-(5-carbamoyl-adamantan-2-yl)-amide hydrochloride of 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid is obtained.

$[M+H^+]=600$; MP=191° C.;

$^1$H NMR (400 MHz, DMSO-d6) δ(ppm)=11.12 (m, 0.5H), 10.38 (m, 0.5H), 8.05 (m, 1H), 7.54 (m, 1H), 7.48 (m, 1H), 7.18 (m, 2H), 6.96 (m, 3H), 6.69 (s; broad, 1H), 6.11 (m, 1H), 4.44 (m, 1H), 3.91 to 3.00 (m, 13H), 2.74 (m, 2H), 2.32 to 1.68 (m, 17H), 1.45 (m, 2H).

The table given below illustrates the chemical structures and the physical properties of some compounds according to the invention, corresponding to formula (I), and being in the form of free bases or of salified compounds:

in column "A", "—" represents a single bond;
base corresponds to the nonsalified molecule
dec. corresponds to a decomposition temperature;
HCl represents a hydrochloride;
Me represents a methyl group;
MP denotes the melting point of the compound, expressed in degrees Celsius;
Salt corresponds to the form of the compound that can be in the form of the base or in salified form, for example a hydrochloride;
$M+H^+$ represents the mass of the compound, obtained by LC-MS (Liquid Chromatography—Mass Spectroscopy).

TABLE (I)

| No | A | $R_{1a}$ | $R_{2a}$ | $R_{1b}$ | $R_{1c}$ | $R_{2c}$ | $R_3$ | $R_4$ | $R_3$ | $R_2$ | $Ar_1$ | $Ar_2$ | Salt | MP (° C.) | $M+H^+$ | Synthesis |
|---|---|---|---|---|---|---|---|---|---|---|---|---|---|---|---|---|
| 1 | — | H | H | H | H | H | H | OH (trans) | —CH$_2$Si(Me)$_3$ | H | pyridine | piperazine-N-R$_8$ | Base | — | 575 | Method 1 |
| 2 | — | H | H | H | H | H | H | OH (trans) | =N—O—C(Me)$_3$ | H | pyridine | piperidine-R$_8$ | Base | 110-113 | 573 | Method 1 |
| 3 | — | H | H | H | H | H | H | OH (trans) | —SO$_2$(CH$_2$)$_2$Si(Me)$_3$ | H | pyridine | piperazine-N-R$_8$ | Base | 107-120 | 653 | Method 1 |
| 4 | — | H | H | H | H | H | H | —CONH$_2$ (trans) | difluorocyclopropyl | H | pyridine | piperazine-N-R$_8$ | Base | 206 | 606 | Method 1 |

TABLE-continued

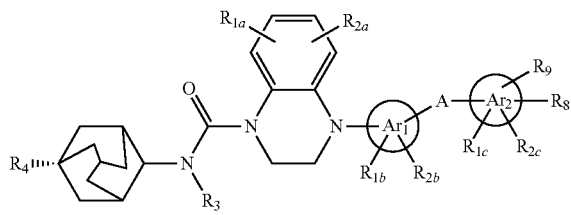

(I)

| No | A | $R_{1a}$ | $R_{2a}$ | $R_{1b}$ | $R_{1c}$ | $R_{2c}$ | $R_3$ | $R_4$ | $R_3$ | $R_2$ | $Ar_1$ | $Ar_2$ | Salt | MP (°C.) | M + H⁺ | Synthesis |
|---|---|---|---|---|---|---|---|---|---|---|---|---|---|---|---|---|
| 5 | — | H | H | H | H | H | H | —CONH₂ (trans) | N-thiomorpholine-1,1-dioxide | H | N-pyridyl—A | A—N-piperidyl-R₈ | Base | 160-200 | 648 | Method 1 |
| 6 | — | H | H | H | H | H | H | —CONH₂ (trans) | HO-CH₂-pyrrolidinyl | H | N-pyridyl—A | A—N-piperidyl-R₈ | HCl | 224 | 614 | Method 2 |
| 7 | — | H | H | H | H | H | H | —CONH₂ (trans) | HO-CH₂-pyrrolidinyl | H | N-pyridyl—A | A—N-piperidyl-R₈ | HCl | 244 | 614 | Method 2 |
| 8 | — | H | H | H | H | H | H | —CONH₂ (trans) | 3-OH-pyrrolidinyl | H | N-pyridyl—A | A—N-piperidyl-R₈ | HCl | 235 | 600 | Method 2 |
| 9 | — | H | H | H | H | H | H | —CONH₂ (trans) | 3-OH-pyrrolidinyl | H | N-pyridyl—A | A—N-piperidyl-R₈ | HCl | 191 | 600 | Method 2 |
| 10 | — | H | H | H | H | H | H | —CONH₂ (trans) | 3,3-F₂-pyrrolidinyl | H | N-pyridyl—A | A—N-piperidyl-R₈ | HCl | 196 | 620 | Method 2 |
| 11 | — | H | H | H | H | H | H | —CONH₂ (trans) | 2,2-F₂-cyclopropyl | H | N-pyridyl—A | A—N-piperidyl-R₈ | HCl | 134-170 | 577 | Method 1 |
| 12 | — | H | H | H | H | H | H | —CONH₂ (trans) | HOOC-cyclopropyl | H | N-pyridyl—A | A—N-piperidyl-R₈ | Base | 145-160 | 585 | Method 1 |
| 13 | — | H | H | H | H | H | H | —CONH₂ (trans) | tetrahydropyridyl | Me | N-pyridyl—A | A—N-Si(R₈)(R₉) | Base | 106-108 | 621 | Method 1 |
| 14 | — | H | H | H | H | H | H | —CONH₂ (trans) | Me | Me | N-pyridyl—A | A—N-Si(R₈)(R₉) | Base | 213-216 | 559 | Method 1 |

The compounds according to the invention have undergone pharmacological tests for determining their inhibitory effect on the enzyme 11βHSD1, which is involved in lipid metabolism and in glucose metabolism.

These tests consisted of measuring the inhibitory activity in vitro of compounds of the invention on the enzyme 11βHSD1 using a Scintillation Proximity Assay (SPA) in 384-well format. The recombinant 1βHSD1 protein was produced in *S. cerevisiae* yeast. The reaction was carried out by incubating the enzyme in the presence of $^3$H-cortisone and NADPH, in the absence or in the presence of increasing concentration of inhibitor. SPA beads coupled to an antimouse antibody, pre-incubated with an anticortisol antibody, made it possible to measure the amount of cortisol formed during the reaction.

The inhibitory activity with respect to the enzyme 11βHSD1 is given by the concentration that inhibits 50% of the activity of 11βHSD1 ($IC_{50}$).

The $IC_{50}$ values of the compounds of the invention are presented in the following table:

| Compound No. | 11βHSD1-HR $IC_{50}$ nM |
|---|---|
| 1 | 7 |
| 2 | 23 |
| 3 | 10 |
| 4 | 3 |
| 5 | 4 |
| 6 | 4 |
| 7 | 3 |
| 8 | 6 |
| 9 | 2 |
| 10 | 2 |
| 11 | 3 |
| 12 | 6 |
| 13 | 25 |
| 14 | 12 |

It therefore appears that the compounds according to the invention have an inhibitory activity on the enzyme 11βHSD1. The compounds according to the invention can therefore be used for preparing medicinal products, in particular medicinal products that are inhibitors of the enzyme 11βHSD1.

Thus, according to another of its aspects, the invention relates to medicinal products that comprise a compound of formula (I), or a salt of addition of the latter with a pharmaceutically acceptable acid or base, or a hydrate or a solvate of the compound of formula (I).

These medicinal products find application in therapeutics, notably in the treatment and prevention of obesity, diabetes, microcirculatory disorders, insulin resistance, metabolic syndrome, Cushing syndrome, hypertension, atherosclerosis, cognition and dementia, glaucomas, osteoporosis, lipodystrophy, cardiac hypertrophy, heart failure, liver diseases, and certain infectious diseases by increasing the effectiveness of the immune system or for promoting wound healing.

According to another of its aspects, the present invention relates to pharmaceutical compositions comprising, as active principle, a compound according to the invention. These pharmaceutical compositions contain an effective dose of at least one compound according to the invention or a pharmaceutically acceptable salt, a hydrate or solvate of said compound, as well as at least one pharmaceutically acceptable excipient. Said excipients are selected, depending on the pharmaceutical form and the desired method of administration, from the usual excipients that are known by a person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or optionally a salt, solvate or hydrate thereof, can be administered as a unit dosage form, mixed with conventional pharmaceutical excipients, to animals and to human beings for preventing or treating the aforementioned disorders or diseases.

The appropriate unit dosage forms comprise forms for administration by the oral route, such as tablets, soft or hard capsules, powders, granules and oral solutions or suspensions, forms for sublingual, buccal, intratracheal, intraocular, intranasal administration, administration by inhalation, forms for topical, transdermal, subcutaneous, intramuscular or intravenous administration, forms for rectal administration and implants. For topical application, the compounds according to the invention can be used in creams, gels, ointments or lotions.

As an example, a unit dosage form of a compound according to the invention in tablet form can comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

According to another of its aspects, the present invention also relates to a method of treatment of the pathologies stated above, comprising the administration, to a patient, of an effective dose of a compound according to the invention, or a pharmaceutically acceptable salt or hydrate or solvate thereof.

The invention claimed is:
1. A compound corresponding to formula (I):

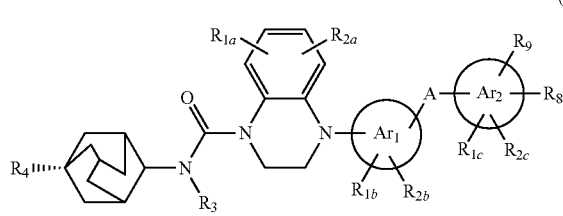

in which:
A represents a bond, an oxygen atom or an —O—CH$_2$— group,
Ar$_1$ represents a phenyl or heteroaryl group,
Ar$_2$ represents a phenyl group, a heteroaryl group or a heterocycloalkyl group,
R$_{1a,1b,1c}$ and R$_{2a,2b,2c}$, which may be identical or different, each represent a hydrogen or halogen atom or an alkyl group; cycloalkyl optionally substituted with an alkyl, haloalkyl, alkoxy-alkyl, alkoxy-haloalkyl or —COOR$_5$ group; -alkyl-cycloalkyl optionally substituted with one or more halogen atoms; —OR$_5$; hydroxy-alkyl; alkoxy-alkyl; alkoxy-alkoxy; haloalkyl; —O-haloalkyl; oxo; —CO-alkyl; —CO-alkyl-NR$_6$R$_7$; —CO-haloalkyl; —COOR$_5$; alkyl-COOR$_5$; —O-alkyl-COOR$_5$; —SO$_2$-alkyl; —SO$_2$-cycloalkyl; —SO$_2$-alkyl-cycloalkyl; —SO$_2$-alkyl-OR$_5$;
—SO$_2$-alkyl-COOR$_5$; —SO$_2$-alkyl-NR$_6$R$_7$; —SO$_2$-haloalkyl; alkyl-SO$_2$-alkyl; —SO$_2$—NR$_6$R$_7$; —SO$_2$-alkyl-alkoxy-alkoxy; —CONR$_6$R$_7$; -alkyl-CONR$_6$R$_7$ or —O-alkyl-NR$_6$R$_7$, or R$_{1a}$, R$_{1b}$, R$_{1c}$ are bound respectively to R$_{2a}$, R$_{2b}$, R$_{2c}$ and to the carbon atom that bears them and represent —O-alkyl-O—;
R$_3$ represents a hydrogen atom or an alkyl group, R₄ represents a hydrogen atom, halogen atom, cyano, —OR₅, hydroxy-alkyl, —COOR₅, —NR₆R₇, —CONR₆R₇, —SO₂-alkyl or —SO₂—NR₆R₇, —NR₆—COOR₅, —NR₆—COR₅, —CO—NR₆-alkyl-OR₅ group;

R₅, R₆ and R₇, which may be identical or different, each represent a hydrogen atom, an alkyl group or an -alkyl-phenyl group, and R₈ represents an alkyl-Si(alkyl)₃; —SO₂-alkyl-Si(alkyl)₃; phenyl; alkoxy-imino; alkyl-cycloalkyl optionally substituted with one or more halogen atoms; heterocycloalkyl substituted with one or more halogen atoms, one or more hydroxy or hydroxy-alkyl groups; or else R₈ and R₉, together with the carbon atom to which they are bound, form a cycloalkyl group optionally substituted with one or more halogen atoms or one or more carboxy groups;

R₉ represents a hydrogen atom or an alkyl group;
or a pharmaceutically acceptable salt thereof of said compound of formula (I).

2. The compound of claim 1, wherein Ar₁ represents a heteroaryl group.

3. The compound of claim 2, wherein Ar₁ represents a pyridinyl group.

4. The compound of claim 1, wherein Ar₂ represents a heterocycloalkyl group.

5. The compound of claim 4, wherein Ar₂ represents a piperidinyl, piperazinyl or azasilinanyl group.

6. The compound of claim 1, wherein R₄ represents a hydroxy or —CONH₂ group.

7. The compound of claim 6, wherein R₈ represents an alkyl-Si(alkyl)₃; —SO₂-alkyl-Si(alkyl)₃; phenyl; alkoxy-imino; heterocycloalkyl substituted with one or more halogen atoms, one or more hydroxy or hydroxy-alkyl groups; or else R₈ and R₉, together with the carbon atom to which they are bound, form a cycloalkyl group optionally substituted with one or more halogen atoms or one or more carboxy groups;

R₉ represents a hydrogen atom or an alkyl group;
provided that when R₈ is an alkyl group, it is attached to the silicon atom of Ar₂.

8. The compound of formula (I) as claimed in claim 1, characterized in that:
A is a direct bond;
Ar₁ is a heteroaryl;
Ar₂ is a heterocycloalkyl;
R₃ represents a hydrogen atom,
R₄ represents an OH or —CONH₂ group,
R₈ represents an alkyl-Si(alkyl)₃; —SO₂-alkyl-Si(alkyl)₃; phenyl; alkoxy-imino; heterocycloalkyl substituted with one or more halogen atoms, one or more hydroxy or hydroxy-alkyl groups; or else R₈ and R₉, together with the carbon atom to which they are bound, form a cycloalkyl group optionally substituted with one or more halogen atoms or one or more carboxy groups;
R₉ represents a hydrogen atom or an alkyl group;
provided that when R₈ is an alkyl group, it is attached to the silicon atom of Ar₂, in the form of base or acid or of salt of addition with an acid or a base.

9. The compound of claim 8, wherein R₈ represents an alkyl-Si(alkyl)₃; —SO₂-alkyl-Si(alkyl)₃; phenyl; alkoxy-imino; pyrrolidinyl optionally substituted with one or more halogen atoms, a hydroxyl or hydroxy-alkyl group; thiomorpholinyl group; or else R₈ and R₉, together with the carbon atom to which they are bound, form a cycloalkyl group optionally substituted with one or more halogen atoms or one or more carboxy groups; and —R₉ represents a hydrogen atom or an alkyl group.

10. The compound of claim 1, wherein A represents a bond.

11. The compound of claim 1, wherein R₁ₐ, R₂ₐ, R₁ᵦ and R₂ᵦ each represent a hydrogen atom.

12. The compound of claim 1, wherein R₃ represents a hydrogen atom.

13. The compound of formula (I) as claimed in claim 1, selected from:
Trans 4-[5-(4-trimethylsilanylmethyl-piperazin-1-yl)-pyridin-2-yl]-3,4-dihydro-2H-quinoxaline-1-carboxylic acid (5-hydroxy-adamantan-2-yl)-amide;
Trans 4-(4-tert-butoxyimino-3,4,5,6-tetrahydro-2H-[1,3']bipyridinyl-6'-yl)-3,4-dihydro-2H-quinoxaline-1-carboxylic acid (5-hydroxy-adamantan-2-yl)-amide;
Trans 4-{5-[4-(2-trimethylsilanyl-ethanesulfonyl)-piperazin-1-yl]-pyridin-2-yl}-3,4-dihydro-2H-quinoxaline-1-carboxylic acid (5-hydroxy-adamantan-2-yl)-amide;
Trans 4-{5-[4-(2,2-difluoro-cyclopropylmethyl)-piperazin-1-yl]-pyridin-2-yl}-3,4-dihydro-2H-quinoxaline-1-carboxylic acid (5-carbamoyl-adamantan-2-yl)-amide;
Trans-6-{6-[4-(5-Carbamoyl-adamantan-2-ylcarbamoyl)-3,4-dihydro-2H-quinoxalin-1-yl]-pyridin-3-yl}-6-aza-spiro[2.5]octane-1-carboxylic acid;
Trans 4-[4-(1,1-dioxo-1lambda6-thiomorpholin-4-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;
Trans 4-[4-((R)-2-hydroxymethyl-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;
Trans 4-[4-((S)-2-hydroxymethyl-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;
Trans 4-[4-((S)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;
Trans 4-[4-((R)-3-hydroxy-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;
Trans 4-[4-(3,3-difluoro-pyrrolidin-1-yl)-3,4,5,6-tetrahydro-2H-[1,3']bipyridinyl-6'-yl]-3,4-dihydro-2H-quinoxaline-1-carboxylic acid (5-carbamoyl-adamantan-2-yl)-amide;
Trans 4-[5-(1,1-difluoro-6-aza-spiro[2.5]oct-6-yl)-pyridin-2-yl]-3,4-dihydro-2H-quinoxaline-1-carboxylic acid (5-carbamoyl-adamantan-2-yl)-amide;
Trans 4-[5-(4-methyl-4-phenyl-[1,4]azasilinan-1-yl)-pyridin-2-yl]-3,4-dihydro-2H-quinoxaline-1-carboxylic acid (5-carbamoyl-adamantan-2-yl)-amide; and
Trans 4-[5-(4,4-dimethyl-[1,4]azasilinan-1-yl)-pyridin-2-yl]-3,4-dihydro-2H-quinoxaline-1-carboxylic acid (5-carbamoyl-adamantan-2-yl)-amide.

14. A pharmaceutical composition comprising the compound of claim 1 or a pharmaceutically acceptable salt thereof; and at least one pharmaceutically acceptable excipient.

15. A method of preparing the compound of claim 1, comprising reacting a compound of formula (IV):

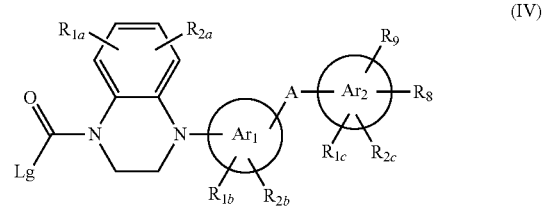

Lg is selected from the group consisting of halogen, mesyl, tosyl, triflate, acetyl, paranitrophenyl, trichloromethoxy, imadazole and methyl-imidazolium; with a compound of formula (V):

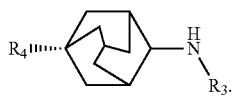

(V)

16. The method according to claim 15 wherein Lg is chloro.

17. The method of preparing the compound of claim 1 in which $Ar_2$ is a piperidine group, A is a single bond joined directly to the nitrogen of the piperidine and $R_8$ is a heterocycloalkyl in position 4 of the nitrogen atom of the piperidine, comprising:

1) transforming a compound of the formula (XXXVII):

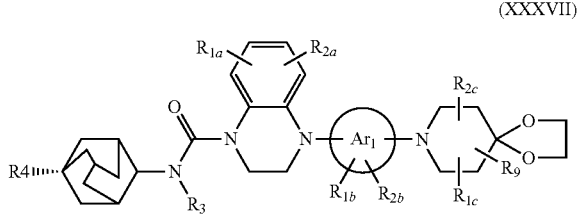

(XXXVII)

by hydrolysis of the acetal function by means of an acid in a solvent to obtain a compound of the formula (XXXIX):

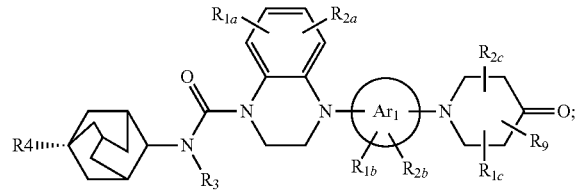

(XXXIX)

and 2) carrying out a reductive amination of the compound of the formula (XXXIX) with a heterocycle having an amine function in the presence of a reducing agent and optionally of an acid to obtain the compound of the formula (XXXVI):

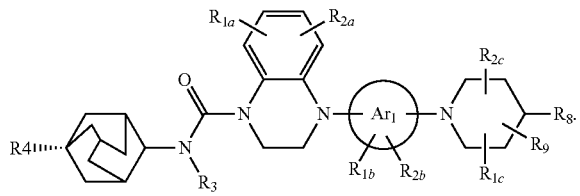

(XXXVI)

18. A method of modulating 11β-hydroxysteroid dehydrogenase type 1 activity in a patient in need thereof comprising administering to said patient a therapeutically effective amount of the pharmaceutical composition of claim 14.

* * * * *